(12) United States Patent
Preston et al.

(10) Patent No.: US 11,281,361 B2
(45) Date of Patent: Mar. 22, 2022

(54) SYSTEM AND METHOD FOR RENDERING A GRAPHICAL USER INTERFACE (GUI) FOR GENERATING A REPORT

(71) Applicant: HealthSnap, Inc., Miami, FL (US)

(72) Inventors: Chase Preston, Miami, FL (US); Yenvy Truong, Lighthouse Point, FL (US)

(73) Assignee: HealthSnap, Inc., Miami, FL (US)

( * ) Notice: Subject to any disclaimer, the term of this patent is extended or adjusted under 35 U.S.C. 154(b) by 0 days.

(21) Appl. No.: 17/139,530

(22) Filed: Dec. 31, 2020

(65) Prior Publication Data
US 2021/0208754 A1    Jul. 8, 2021

Related U.S. Application Data

(60) Provisional application No. 62/956,927, filed on Jan. 3, 2020.

(51) Int. Cl.
| | |
|---|---|
| *G06F 3/0484* | (2013.01) |
| *G06F 9/451* | (2018.01) |
| *G16H 15/00* | (2018.01) |
| *G06Q 10/10* | (2012.01) |
| *G16H 10/60* | (2018.01) |

(52) U.S. Cl.
CPC ............ *G06F 3/0484* (2013.01); *G06F 9/453* (2018.02); *G06Q 10/10* (2013.01); *G16H 10/60* (2018.01); *G16H 15/00* (2018.01)

(58) Field of Classification Search
CPC ....... G06F 9/453; G06F 3/0484; G06Q 10/10; G06Q 40/08; G06Q 50/22; G06Q 10/06316; G16H 40/20; G16H 15/00; G16H 10/60
See application file for complete search history.

(56) References Cited

U.S. PATENT DOCUMENTS

| | | | |
|---|---|---|---|
| 2016/0162459 A1* | 6/2016 | Parker | G06Q 50/26 715/226 |
| 2018/0204438 A1* | 7/2018 | Cullin | G08B 25/009 |
| 2018/0240547 A1* | 8/2018 | Albert | G16H 40/20 |
| 2019/0333631 A1* | 10/2019 | Meng | A61B 5/0205 |

* cited by examiner

*Primary Examiner* — Nicholas Ulrich
(74) *Attorney, Agent, or Firm* — Sterne, Kessler, Goldstein & Fox P.L.L.C.

(57) ABSTRACT

Described herein is a system for rendering a graphical user interface (GUI) for generating an report. In an embodiment, a central system may generate and render a first screen of a graphical user interface (GUI), including names of one or more users, and a first status corresponding to a first type of predefined action for each of the one or more users. The central system may further generate and render a second screen of the GUI including a second status corresponding to a second type of predefined action for each of the one or more users. The central system may further render generate and render a third screen of the GUI including a third status corresponding to a third type of predefined action.

20 Claims, 21 Drawing Sheets

FIG. 1

In-Progress
March 2019 RPM Eligibility Report 📎 Data Transmission ⊕ Treatment ✂ Set Up 99454: Remote monitoring of physiologic parameter(s) (eg, weight, blood pressure, pulse oximetry, respiratory flow rate), initial; device(s) supply with daily recording(s) or programmed alert(s) transmission, each 30 days.

| Search | | STATUS<br>Show All ▼ | LAST DATA<br>Show All ▼ | TRANSMISSION INDEX<br>Past 30 days ▼ |
|---|---|---|---|---|
| Blanche Terry<br>05-04-1975<br>(888) 888-1929 | Dr. John Smith | Eligible | 2 day ago | 60% — View Calendar |
| Jennie Ellis<br>05/04/1975<br>(888) 888-1929 | Dr. Jenny Turner | Eligible — Eligible on 16 March, 2019 | Yesterday | 52% — View Calendar |
| George Caldwell<br>05/04/1975<br>(888) 888-1929 | Dr. John Smith | Not Eligible — Pending 16 days data transmission with a 30 day period | 2 days ago | 45% — View Calendar |
| Hatties Summers<br>05/04/1975<br>(888) 888-1929 | Dr. John Smith | Not Eligible — Pending 16 days data transmission with a 30 day period | 3 days ago | 20% — View Calendar |
| Daisy Gill<br>05/04/1975<br>(888) 888-1929 | Dr. Jenny Turner | Not Eligible — Pending 16 days data transmission with a 30 day period | 4 days ago | 10% — View Calendar |
| Pauline Gibson<br>05/04/1975<br>(888) 888-1929 | Dr. John Smith | Not Eligible — Pending 16 days data transmission with a 30 day period | 3 days ago | 5% — View Calendar |
| Edna Aguilar<br>05/04/1975<br>(888) 888-1929 | Dr. Jenny Turner | Not Eligible — Pending 16 days data transmission with a 30 day period | 10 days ago | 5% — View Calendar |

Showing 7 of 7     Show 10 per page

Eligible on 28 March, 2019

Review & Submit
March 2019 RPM Eligibility Report — Review eligible patients for 99454 (data transmission) ← 402

| | | STATUS Show All ▼ | |
|---|---|---|---|
| Blanche Terry 05-04-1975 (888) 888-1929 ← 432 | Dr. John Smith | Eligible | Eligible on 28 March, 2019 |
| Jennie Ellis 05/04/1975 (888) 888-1929 | Dr. Jenny Turner | Eligible | Eligible on 16 March, 2019 | View Calendar |
| George Caldwell 05/04/1975 (888) 888-1929 | Dr. John Smith | Eligible | Eligible on 15 March, 2019 | View Calendar |
| Hatties Summers 05/04/1975 (888) 888-1929 | Dr. John Smith | Eligible | Eligible on 2 March, 2019 | View Calendar |
| Daisy Gill 05/04/1975 (888) 888-1929 | Dr. Jenny Turner | Eligible | Eligible on 23 March, 2019 | View Calendar |
| Pauline Gibson 05/04/1975 (888) 888-1929 ← 433 | Dr. John Smith | Not Eligible | Insufficient data transmission | View Calendar |
| Edna Aguilar 05/04/1975 (888) 888-1929 | Dr. John Smith | Not Eligible | Insufficient data transmission ← 434 | View Calendar |

Showing 7 of 7 — Show 10 per page ← 436

○ Check the box agree to statement about agreeing to the above being true and signing electronically

[ NEXT > ] ← 438

Review & Submit
March 2019 RPM Eligibility Report — 424

Review eligible patients for 99453 (setup)

| | | | STATUS<br>Show All ▼ | |
|---|---|---|---|---|
| 🧑 | Blanche Terry<br>05-04-1975<br>(888) 888-1929 | Dr. John Smith | (Eligible) | Eligible on 28 March, 2019 |
| 🧑 | Jennie Ellis<br>05/04/1975<br>(888) 888-1929 | Dr. Jenny Turner | (Eligible) | Eligible on 16 March, 2019 |
| 🧑 | George Caldwell<br>05/04/1975<br>(888) 888-1929 | Dr. John Smith | (Eligible) | Eligible on 15 March, 2019 |
| 🧑 | Hatties Summers<br>05/04/1975<br>(888) 888-1929 | Dr. John Smith | (Eligible) | Eligible on 2 March, 2019 |
| 🧑 | Daisy Gill<br>05/04/1975<br>(888) 888-1929 | Dr. Jenny Turner | (Not Eligible) | Insufficient data transmission |
| 🧑 | Pauline Gibson<br>05/04/1975<br>(888) 888-1929 | Dr. John Smith | (Not Eligible) | Insufficient data transmission |
| 🧑 | Edna Aguilar<br>05/04/1975<br>(888) 888-1929 | | | — 444 |

442 ↗  443 ↗

Showing 7 of 7                                              Show 10 per page

◉ Check the box agree to statement about agreeing to the above being true and signing electronically < BACK                                                                    NEXT > — 446

Download as PDF

March 2019 RPM Eligibility Report
Submitted 4 April, 2019 by NAME — 402

SUMMARY REPORT — 414

| | | 99454 | 99453 | 99457 | |
|---|---|---|---|---|---|
| Blanche Terry<br>05-04-1975<br>(888) 888-1929 | Dr. John Smith | Eligible | Eligible | Eligible | View |
| Jennie Ellis<br>05/04/1975<br>(888) 888-1929 | Dr. Jenny Turner | Eligible | Eligible | Eligible | View |
| George Caldwell<br>05/04/1975<br>(888) 888-1929 | Dr. John Smith | Eligible | Eligible | Not Eligible<br>Insufficient<br>treatment time | View |
| Hatties Summers<br>05/04/1975<br>(888) 888-1929 | Dr. John Smith | Eligible | Eligible | Not Eligible<br>Insufficient<br>treatment time | View |
| Daisy Gill<br>05/04/1975<br>(888) 888-1929 | Dr. Jenny Turner | Not Eligible<br>Insufficient data<br>transmission | Eligible | Not Eligible<br>Insufficient<br>treatment time | View |
| Pauline Gibson<br>05/04/1975<br>(888) 888-1929 | Dr. John Smith | Not Eligible<br>Insufficient data<br>transmission | Not Eligible<br>Previously<br>eligible | Not Eligible<br>Insufficient data<br>transmission | View |
| Edna Aguilar<br>05/04/1975<br>(888) 888-1929 | | | | | |

Showing 7 of 7 — Show 10 per page

550

HealthSnap Clinic

HealthSnap | ≡ HealthSnap Clinic | 📱 | 👥 | ⋮⋮⋮ | 🔍 Search Patients | + | 🔔 | ❓ | ⬇

< TestText  (Live)(RPM) Updated 5 days ago    Collection Hub | Add Note | Send Visit Request
1234

General | Lifestyle Profile | Collection Log | Tracking | Messages | Recommendations

DEMOGRAPHICS                                                    [Edit]

DATE OF BIRTH    GENDER    PHONE                ETHNICITY
11/25/1998       Male      (305)245-6543        Caucasian/White
(22 years old)             jtestc11252@gmail.com Hispanic/Latino ADDRESS
3635 NE 1st Ave, Apt 809

MEDICAL HISTORY                                                 [Edit]

SMOKING
Non-Smoker

CONNECTED DEVICES [Add Device]

♡ Apple Health

NOTES                                                           ← 552
Showing 1 of 1 [View All] [+ Add Note]

Add 5 minutes
• Administrative [+5 min (November, 2020)]  Submitted Nov 30, 2020, 11:26 AM by John Smith   [Edit] [Delete]
                                             Edited Nov 30, 2020, 11:27 AM by John Smith
                                                                                        ← 554

[Disconnect with patient] ← 556

In-Progress
November 2020 RPM Eligibility Report

| Data Transmission | Treatment | Set Up |

99457/99458: Remote physiologic monitoring treatment management services, clinical staff/physician/other qualified healthcare professional time in a calendar month regarding interactive communication with the patient/caregiver during the month, initial 20 minutes/additional 20 minutes

| | Order Provider (View All) | 99457 Status (View All) | 99458 Status (View All) | Time Spent (View All) |
|---|---|---|---|---|
| Search | | | 562 | |
| Android 21 OS 8.1 3242 07/29/1968 | Chase Preston | Not Eligible Insufficient data transmission | Not Eligible Insufficient data transmission | 10 min (+Add) |
| Caroline Fleisher 09/04/1990 | Dr. John Smith | Not Eligible Insufficient data transmission | Not Eligible Insufficient data transmission | 10 min (+Add) |
| Charles Preston 03/05/01995 | Chase Preston | Not Eligible Insufficient data transmission | Not Eligible Insufficient data transmission | 10 min (+Add) |
| Charlie Przwoski SALESFORCECLHARLIE 09/15/1975 | Dr. John Smith | Not Eligible Insufficient data transmission | Not Eligible Insufficient data transmission | 10 min (+Add) |
| Chase Preston 05/04/1989 | Chase Preston | Not Eligible Insufficient data transmission | Not Eligible Insufficient data transmission | 0 min (+Add) |
| Chase Preston 02/12/1986 | Chase Preston | Not Eligible Insufficient data transmission | Not Eligible Insufficient data transmission | 0 min (+Add) |
| Chase Preston 05/04/1975 | Chase Preston | | | 0 min (+Add) |

Showing 10 of 69    Previous 1 2 3 4 5 6 7 Next    Show 10 per page 561, 560, 564

SYSTEM AND METHOD FOR RENDERING A GRAPHICAL USER INTERFACE (GUI) FOR GENERATING A REPORT

CROSS-REFERENCE TO RELATED APPLICATIONS

This application claims priority to U.S. Provisional Application No. 62/956,927, filed on Jan. 3, 2020, the contents of which are incorporated herein by reference in their entirety.

BACKGROUND

Systems may trigger predefined actions for a user based on received data transmissions. Tracking data transmissions and determining eligibility for triggering the predefined actions may be a complex process. The frequency of data transmissions from various users may be erratic and voluminous. This causes errors and inconsistencies in triggering the predefined actions.

BRIEF DESCRIPTION OF THE DRAWINGS

The accompanying drawings, which are incorporated herein and form a part of the specification, illustrate the embodiments of the present disclosure, and together with the description, further serve to explain the principles of the embodiments and enable a person skilled in the pertinent art to make and use the embodiments, individually, or as a combination thereof.

FIG. 1 is an example patient profile GUI according to an example embodiment.

FIGS. 4A-4H are example GUIs illustrating eligibility reports according to an example embodiment.

FIGS. 5A-5D are example GUIs allowing users to input an amount of time that healthcare was provided to a patient, according to an example embodiment.

In the drawings, like reference numbers generally indicate identical or similar elements. Additionally, generally, the left-most digit(s) of a reference number identifies the drawing in which the reference number first appears.

DETAILED DESCRIPTION

Figure 2A:
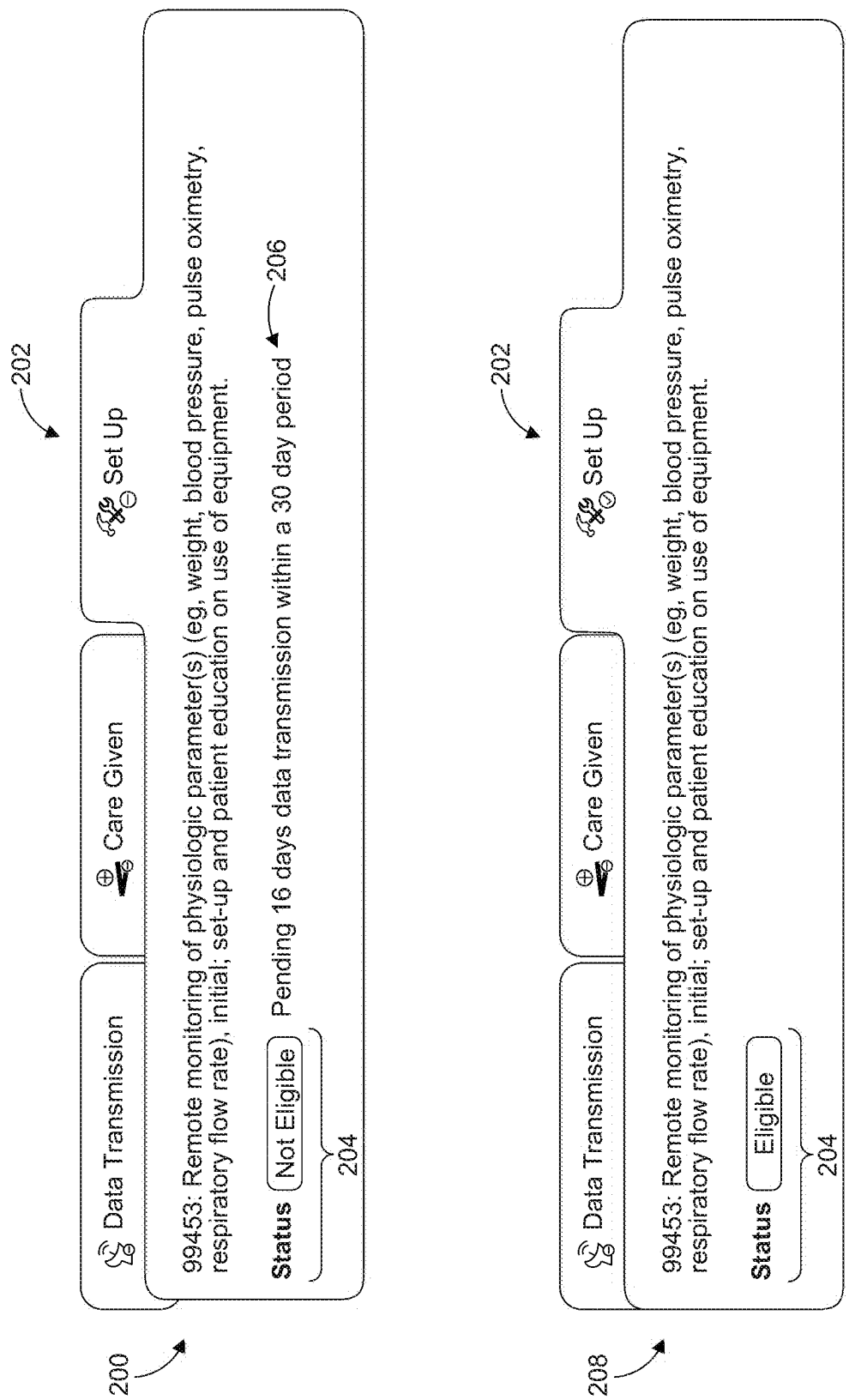
FIGS. 2A-2D are example GUIs indicating a reimbursement eligibility status according to an example embodiment.

Described herein is a system for rendering a graphical user interface (GUI) for generating a report. As stated above, systems may keep track of data transmissions for triggering eligibility for predefined actions. The eligibility may be of different types of predefined actions. Each of the types of eligibility may be triggered based on different reasons. The data transmissions may be from various users and may be erratic and voluminous. The system described herein generates a GUI for tracking data transmissions and generating eligibility reports based on the data transmissions.

In an embodiment, a central system may generate and render a first screen of a graphical user interface (GUI), including names of one or more users, a first status corresponding to a first type of predefined action for each of the one or more users, and a selector to view a calendar for each of the one or more users. The central system may further generate and render a second screen of the GUI, including each of the one or more users' names and a second status corresponding to a second type of predefined action for each of the one or more users. The second screen is rendered in response to receiving a first input indicating verification of the first status for each of the one or more users. The central system may further generate and render a third screen of the GUI including each of the one or more users' names, a third status corresponding to a third type of predefined action for each of the one or more users, and an indication of whether a qualifying factor for the third status has been satisfied for each one of the one or more users. The third screen is rendered in response to receiving a second input indicating verification of the second status for each of the one or more users. The central system may generate and render a summary screen of the GUI, including the first, second, and third statuses for each of the one or more users.

By visually keeping track of the data transmissions and eligibility for triggering predefined actions, the system eliminates possible errors or inconsistencies in triggering predefined actions for a given user.

Figure 1:
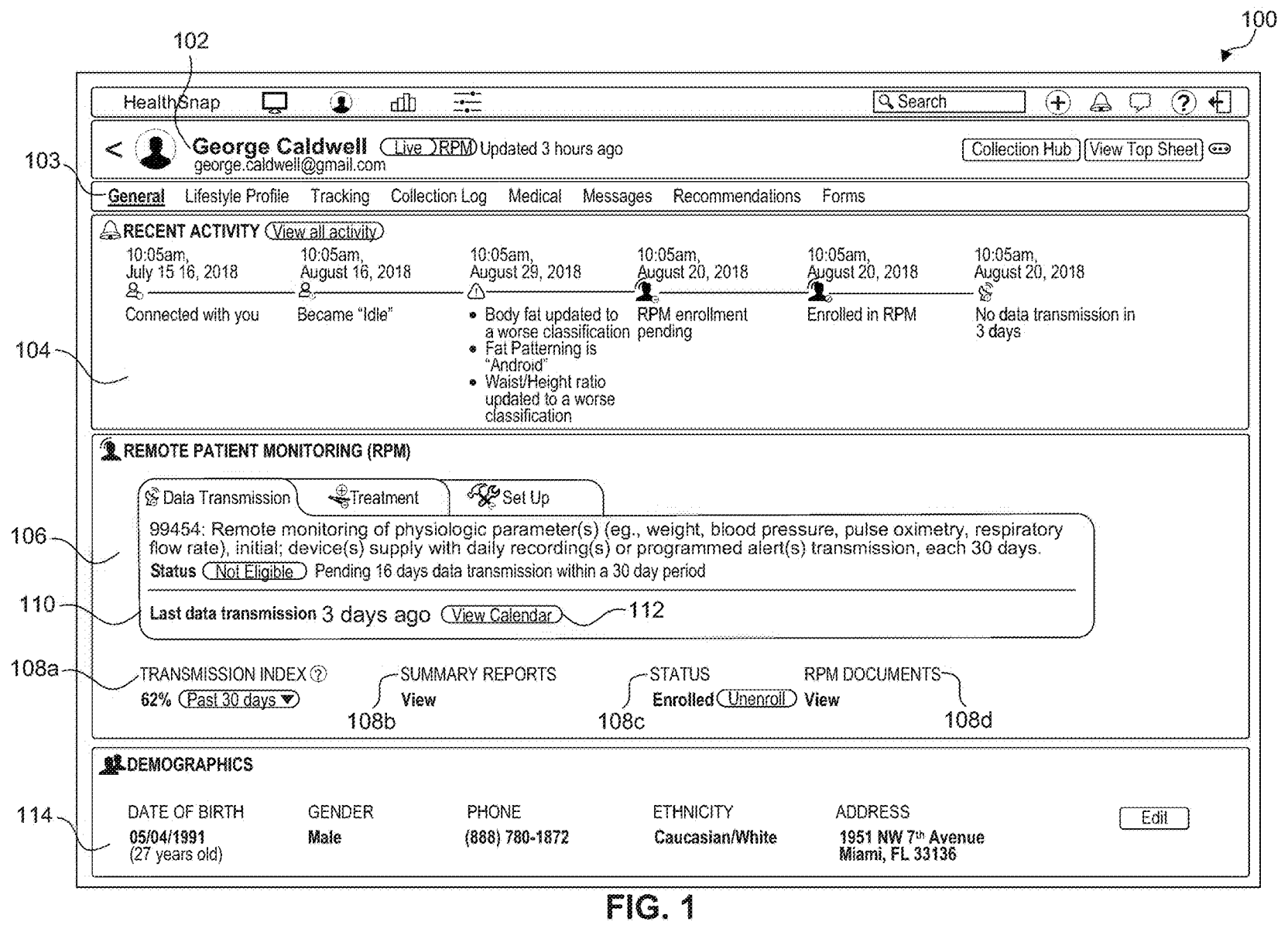

FIG. 1 is an example user profile GUI 100 according to an example embodiment. The user profile GUI 100 may provide user information to an entity implementing the system for generating an eligibility report. The user profile GUI 100 may be rendered on a portal provided to and/or accessed by the entity.

As a non-limiting example, the entity may be a healthcare provider, and the user may be a patient. The user profile GUI 100 may be accessed using the portal. The user profile GUI 100 may include information about a patient signed up for remote patient monitoring (RPM). RPM may allow healthcare providers to remotely monitor patients to become eligible for reimbursements such as data transmission reimbursement, treatment reimbursement, and set up reimbursement. The patient profile 100 may include data associated with the patient such as, for example, and without limitation, the patient's name 102, a recent activity section 104, an RPM section 106, and a demographics section 114. The user profile GUI 100 may also include tabs 103, including, for example, and without limitation, general, lifestyle profile, tracking, collection log, medical, messages, recommendations, and forms.

The recent activity section 104 may include a timeline of activity for the patient. The timeline may range from enrollment for RPM to the date of the last data transmission. The timeline of activity may also include alerts related with the patient's health.

The RPM section 106 may include a summary 110 of the reimbursement eligibility. In particular, summary 110 may include tabs for summaries for the data transmission reimbursement, treatment reimbursement, and set up reimbursement. The tab for the data transmission reimbursement may include reimbursement eligibility status, the days since the last data transmission, and a view calendar button 112. In response to selecting the view calendar button 112, a graphical user interface (GUI) indicating eligibility for triggering action may be rendered. The visual representation of the calendar may be displayed in the foreground while the user profile GUI 100 may remain in the background.

The tab for treatment (not shown) may include treatment reimbursement eligibility status and a button to confirm that healthcare has been provided for a certain amount of time. For example, the healthcare provider may confirm that 20 minutes or more of clinical staff/physician/other qualified healthcare professional time in a calendar month have been provided. If the healthcare provider has confirmed that 20 minutes or more of interactive communication was spent with the patient, the tab for treatment may include a date and time of the confirmation and a button to un-confirm that 20 minutes or more of interactive communication was spent with the patient. The tab for set up (not shown) may include a set up eligibility status.

The RPM section 106 may also include transmission index section 108*a*, summary reports section 108*b*, status section 108*c*, and RPM documents section 108*d*. The transmission index of section 108*a* is a measure of the frequency of data transmission by a patient. The transmission index may be calculated by dividing the number of days of data transmission by a total number of days the patient has been enrolled in RPM. For example, if in the past 30 days data transmissions were received from the patient on 12 days, the transmission index for the past 30 days would be calculated as follows: (12/30)*100=40%. The transmission index may be calculated for the past 30 days, 3 months, 6 months, 1 year, or total time of enrollment. A user may select the amount of time for calculating the transmission index in section 108*a* using a dropdown menu.

The summary reports section 108*b* may include a link to view all summary reports for the patient. A summary report includes a list of data collection, any notes made that month, any messages sent, a snapshot of their lifestyle profile, insurance information, any recommendations sent, patient information, and/or the like. This may be a PDF file that can be uploaded to the healthcare provider's billing system.

The status section 108*c* indicates an enrollment status of the patient. A healthcare provider may select to un-enroll the patient using an un-enroll button positioned next to the enrollment status.

The RPM documents section 108*d* may include a link to view all RPM documents for a patient, such as insurance information, reason, diagnosis, consent forms, and/or the like.

The demographics section 114 may include patient information such as date of birth, gender, phone number, ethnicity, address, and/or the like.

FIGS. 2A-2D are example GUIs indicating an eligibility status according to an example embodiment. As a non-limiting example, the eligibility status may correspond to a reimbursement eligibility status. FIGS. 2A-2D will be described herein concurrently. As described with respect to FIG. 1, the patient profile GUI may include a reimbursement status summary. The reimbursement status summary may include a reimbursement eligibility status for data transmission reimbursement, treatment reimbursement, and set up reimbursement. Data transmission reimbursement eligibility, treatment reimbursement eligibility, and set up reimbursement eligibility may be determined by an eligibility determination system. Such an eligibility determination system determines eligibility status for each patient individually, and that status data is used to generate the eligibility reports. Example processes and systems for determining eligibility status are disclosed in U.S. Provisional Patent Appl. No. 62/956,918, filed on Jan. 3, 2020 and U.S. Non-Provisional patent application Ser. No. 17/139,534 filed concurrently herewith, which is incorporated herein by reference in its entirety.

With reference to FIG. 2A, a GUI 200 including a set up reimbursement eligibility status summary 202 is illustrated. The set up reimbursement eligibility summary 202 may include an eligibility status 204. In the example presented in FIG. 2A, the eligibility status 204 in GUI 200 is "Not Eligible". GUI 200 may include a reason 206 for the eligibility status 204 being "Not Eligible". For example, a healthcare provider may only be eligible for the set up reimbursement in response to receiving a first data transmission from a patient enrolled in RPM. The reason 206 may explain that the patient has not yet also transmitted a minimum threshold number of days within a given time window in a first instance. In another example, in a GUI 208, including set up reimbursement eligibility summary 202, a different eligibility status 204 is illustrated. In this example, the eligibility status 204 in GUI 208 indicates "Eligible".

Figure 2B:
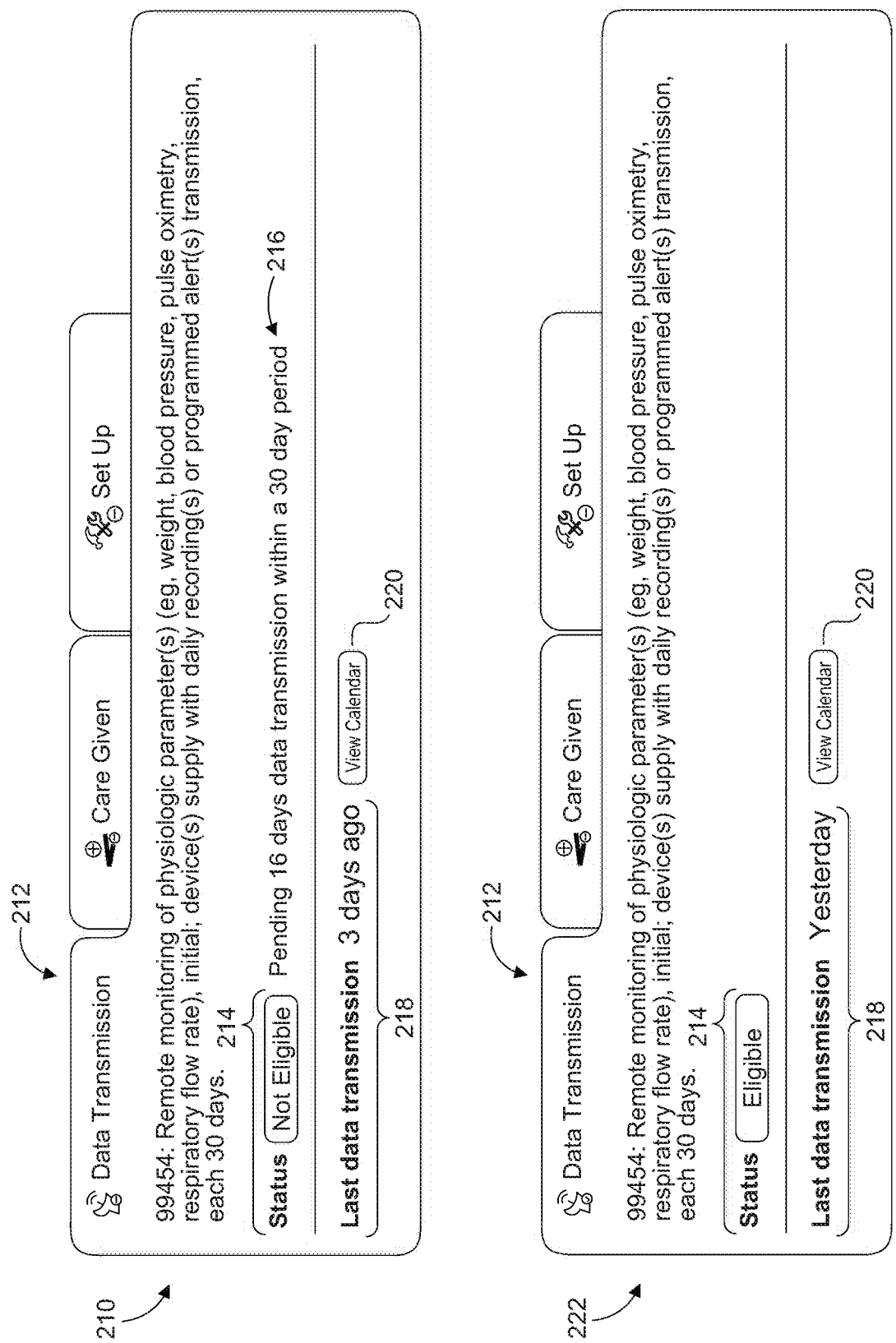

With reference to FIG. 2B, a GUI 210 including a data transmission reimbursement eligibility status summary 212, is illustrated. The data transmission reimbursement eligibility status summary 212 may include an eligibility status 214, an amount of time 218 since the last data transmission, and a view calendar button 220. In the example presented in FIG. 2B, the eligibility status 214 in GUI 210 is "Not Eligible". A reason 216 may be rendered adjacent to the eligibility status 214. For example, a healthcare provider may be eligible for the data transmission reimbursement in response to a patient transmitting data on at least a minimum threshold number of days within a given time window and after a specified amount of time has passed since the last data transmission reimbursement eligibility was triggered or since the patient enrolled in RPM. In the example of GUI 210, the reason 216 is given as "Pending 16 days of data transmissions in a 30 day period." In this example, 16 days is the required minimum threshold number of days with data transmissions from the patient, while the 30 days is the given time window. As a non-limiting example, the amount of time 218 since the last data transmission may be a number of days (e.g., 3 days). In response to selecting the view calendar button 220, a calendar indicating the data transmissions in a calendar month (or given time window) for a patient may be rendered. In GUI 222, the data transmission reimbursement eligibility status summary 212 may include an eligibility status 214, an amount of time 218 since the last data transmission, and a view calendar button 220. In the example of GUI 222, the eligibility status is "Eligible", and the amount of time since the last data transmission indicates "Yesterday".

Figure 2C:
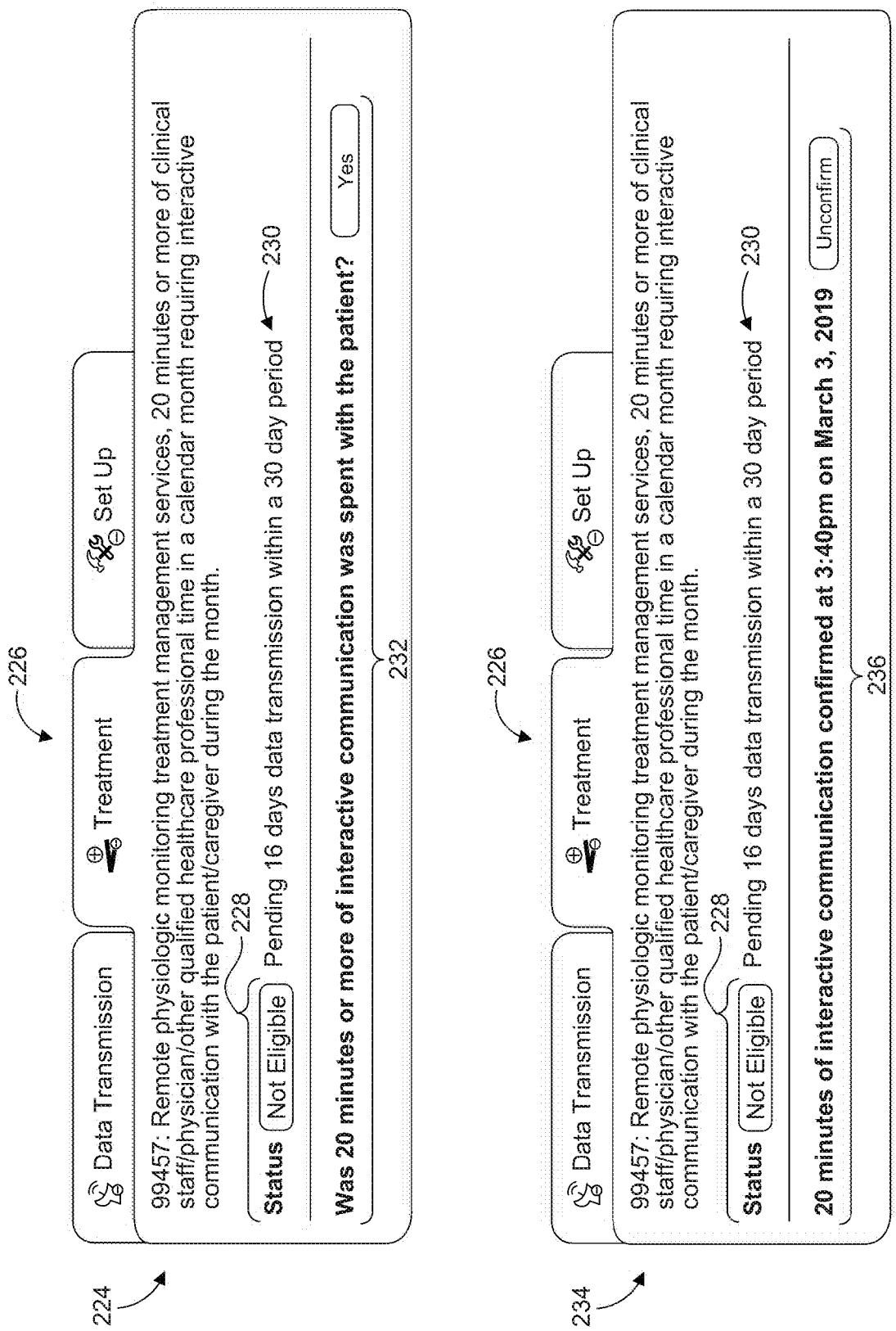

With reference to FIG. 2C, a GUI 224, including a treatment reimbursement eligibility status summary 226, is illustrated. The treatment reimbursement eligibility status summary 226 includes an eligibility status 228 and a confirmation button 232 of whether a specified amount of treatment was provided. In the example of GUI 224, the eligibility status 228 is "Not Eligible". A reason 230 for the eligibility status 228 being "Not Eligible" may be rendered adjacent to the eligibility status 228. For example, the healthcare provider may be eligible for treatment reimbursement in response to a healthcare provider spending a specified amount of time of interactive communication with the patient during the given time window. In the example of GUI 224, the reason 230 reads "Pending 16 days data transmission within a 30 day period." The confirmation button 232 may allow a healthcare provider to confirm that a specified amount of time of interactive communication was spent with the patient. The specified amount of time may be, for example, 20 minutes. A message may be rendered adjacent to the confirmation button 232. In the example of GUI 224, the message reads, "Was 20 minutes or more of interactive communication was spent with the patient?" The confirmation button 232 may read "Yes".

In GUI 234, the treatment reimbursement eligibility status summary 226 includes an eligibility status 228 and an unconfirmation button 232. In the example of GUI 234, the eligibility status 228 is "Eligible". The unconfirmation button 232 may be selected to reverse the confirmation that a specified amount of time of interactive communication was spent with the patient on a given date.

Figure 2D:
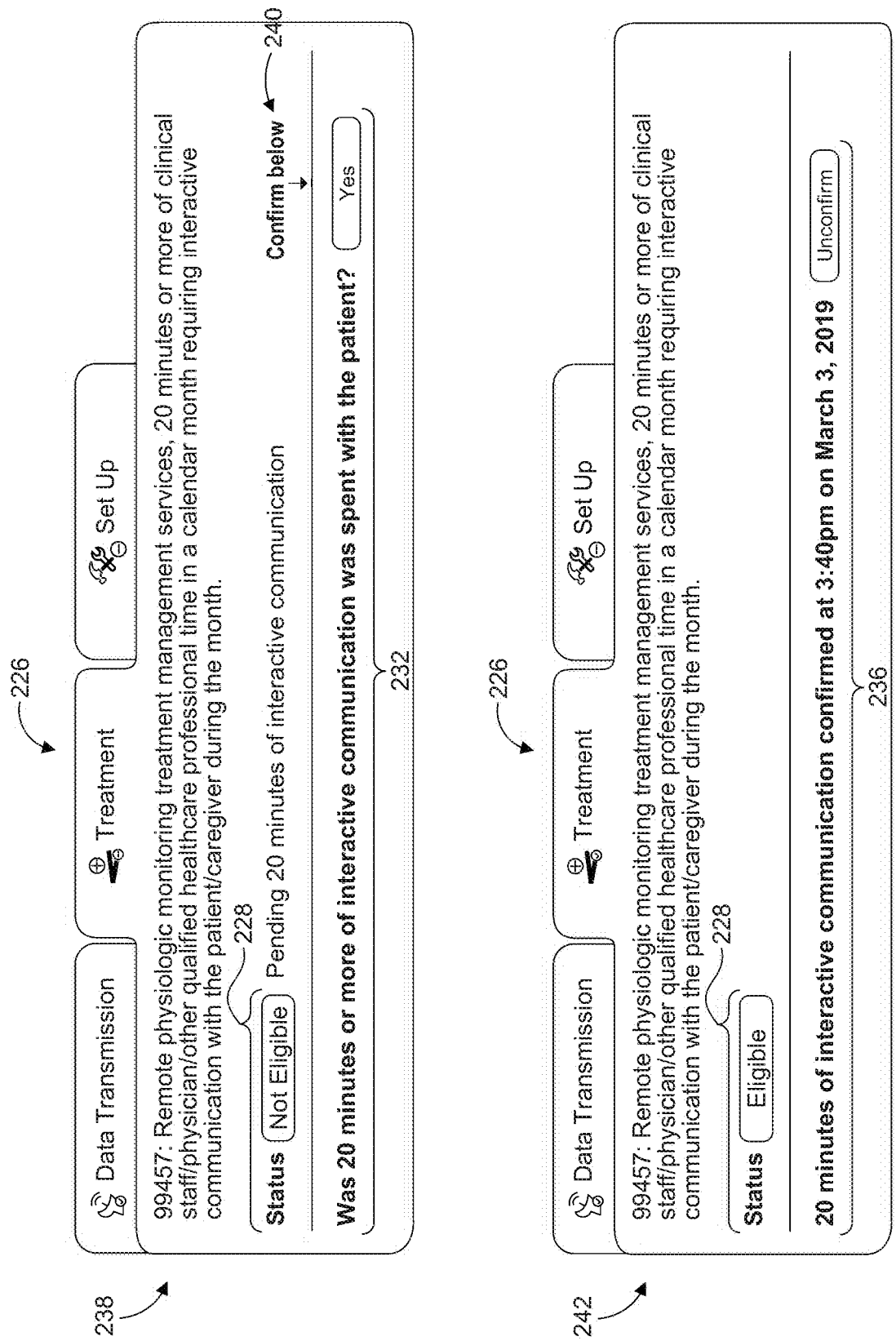

With reference to FIG. 2D, a GUI 238, including a treatment reimbursement eligibility status summary 226, is illustrated. The treatment reimbursement eligibility status summary 226 includes an eligibility status 228 and a confirmation button 232 of whether a specified amount of treatment was provided. In the example presented in FIG. 2D, the eligibility status 228 in GUI 224 is "Not Eligible". A reason for the eligibility status 228 being "Not Eligible" may be rendered adjacent to the eligibility status 228. For example, as described above, the healthcare provider may be eligible for the treatment reimbursement in response to a healthcare provider providing a specified amount of time of interactive communication with the patient in the given time window. The patient may have provided the minimum threshold number of days with data transmissions within a given time window, but a healthcare provider may not have provided a specified amount of time of interactive communication with the patient in the given time window. The reason may read "Pending 20 minutes of interactive communication." The reason may further include an instruction 240 to confirm the communication. In the example of GUI 238, instruction 240 includes an arrow to the confirmation button 232.

Figure 3:
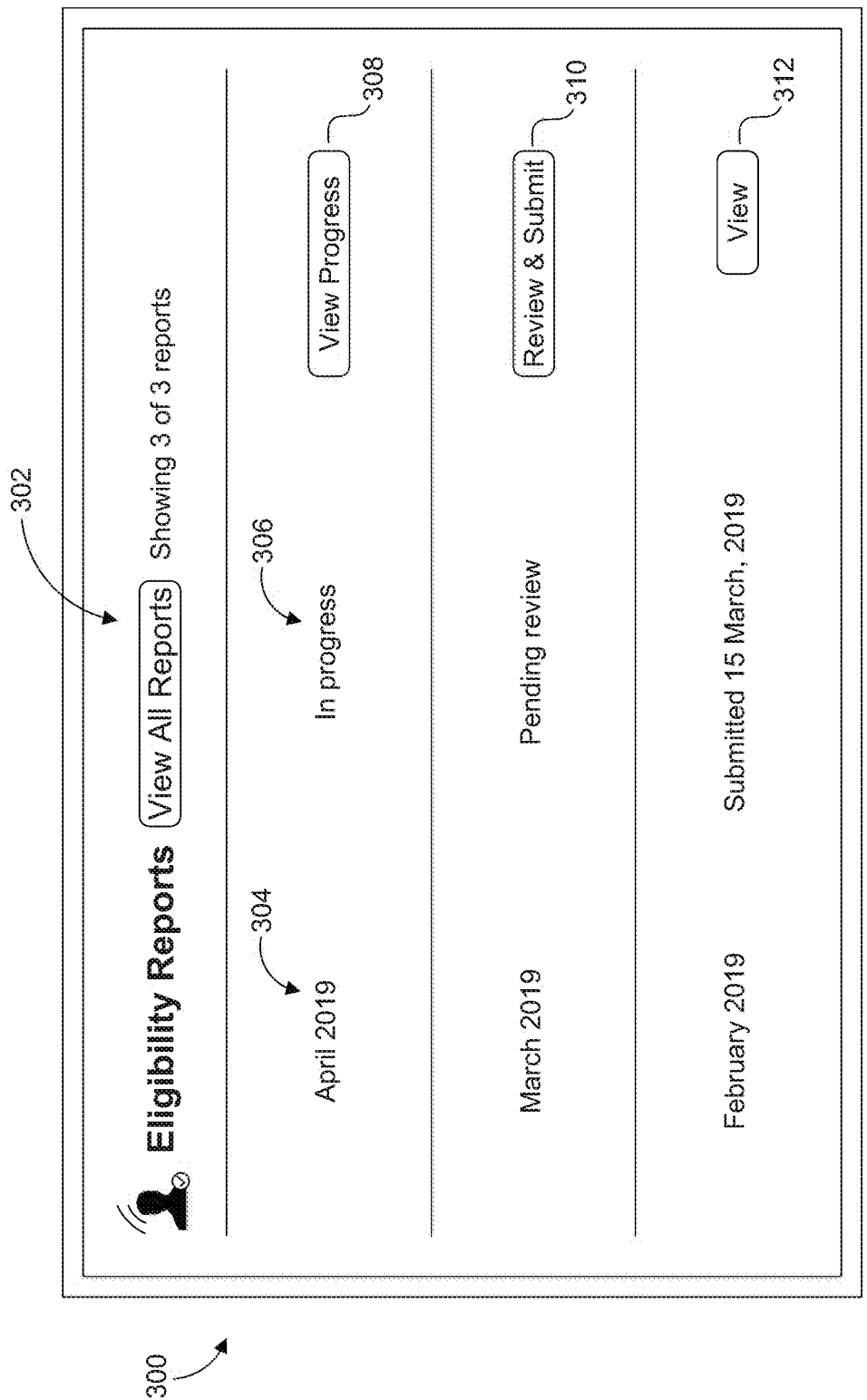
FIG. 3 is an example GUI showing a list of months with eligibility reports according to an example embodiment.

FIG. 3 is an example GUI 300, including a list of months with eligibility reports according to an example embodiment. The GUI 300 may be rendered on a healthcare provider portal. The healthcare provider may interact with GUI 300 to view eligibility reports for all associated patients for a given calendar month. The eligibility report may indicate the reimbursement eligibility for each of the patients in a given month.

The GUI 300 may include a view all reports button 302, a list of months 304, and a status 306 for each eligibility report. In response to selecting the view all reports button 302, a healthcare provider may view all of the eligibility reports for all the available months. An eligibility report may be submitted at the end of each calendar month. The status 306 of an eligibility report may be, for example, and without limitation, "In-Progress", "Pending Review", or "Submitted" on a given date. The status 304 of the eligibility report for a current month will typically be "In-Progress". The "Pending Review" status may correspond to a completed month for which an eligibility report has not been submitted. The "Submitted" status may correspond to a completed month for which an eligibility report has already been submitted.

The GUI 300 may also include a "View Progress" button 308 corresponding to a month with an "In-Progress" status. In response to selecting a "View Progress" button 308, a popup may be rendered showing the patients enrolled in RPM and their progress towards being eligible for set up, data transmission, or treatment reimbursement. The popup may be rendered within the same tabs as the patient profile GUI, including each code and status of each patient.

The GUI 300 may also include a "Review & Submit" button 310 corresponding to a month with a "Pending Review" status. On the last day of a calendar month, the status "In-Progress" changes to "Ready for Review" or "Pending Review". The provider may select the "Review & Submit" button 310 to review eligibility reports and submit the eligibility reports. In response to selecting the "Review & Submit" button 310, a popup may be rendered, and a healthcare provider may complete the steps of reviewing and submitting the eligibility reports.

The GUI 300 may also include a "View" button 312 corresponding to a month for which an eligibility report has been submitted. In response to selecting the "View" button 312, a popup may be rendered, including the submitted eligibility report.

FIGS. 4A-H are example GUIs illustrating eligibility reports according to an example embodiment. FIGS. 4A-H will be described herein concurrently. As described above, eligibility reports may be generated for each calendar month. The eligibility report may be submitted after, for example, the last day of the calendar month. Once the eligibility report is submitted, the values associated with each patient's reimbursement eligibility status are committed in a database, and healthcare providers are provided read-only access. The values may not be altered. The eligibility reports may be used to trigger a first, second, and third type of predefined actions. The first, second, and third type of predefined actions may correspond with a reimbursement request. The first type of predefined action may correspond with a data transmission reimbursement. The second type of predefined action may correspond with a set up reimbursement. The third type of predefined action may correspond with a treatment reimbursement. It can be appreciated that the reports for the data transmission reimbursement, set up reimbursement, or treatment reimbursement may be rendered in any order.

With reference to FIG. 4A, in response to selecting the "View Progress" button as described above, a pop up 400 may be rendered. The pop up 400 may include a progress report GUI for the data transmission reimbursement 402 for each of the healthcare provider's patients. The progress report GUI for the data transmission reimbursement 402 may include a list of the patients' names, date of birth, and phone number in a first column 404, the ordering provider in a second column 405, the eligibility status for each respective patient in a third column 406, an amount of time since the last data transmission in a fourth column 406, a transmissions index in the fifth column 409, and a view calendar button for each in a sixth column 410. The eligibility status may be, for example, and without limitation, "Eligible" or "Not Eligible". A healthcare provider may be eligible for a data transmission reimbursement for a patient in response to a patient transmitting data a minimum threshold number of days within a given time window, after a specified amount of time has passed since the last data transmission reimbursement eligibility was triggered or since the patient enrolled in RPM. In the event the healthcare provider is not eligible for a data transmission reimbursement for a given patient, a text-based reason may be rendered adjacent to the eligibility status in the third column 406. The transmissions index may be calculated by determining the percentage of days having data transmissions over a period of time for each patient. In the event the healthcare provider is eligible for a data transmission reimbursement for a given patient, a date when eligibility was triggered may be rendered adjacent to the eligibility status in the third column 406. In response to selecting the view calendar button in the sixth column 410, a calendar indicating the data transmissions in a calendar month for a patient may be rendered.

Figure 4B:
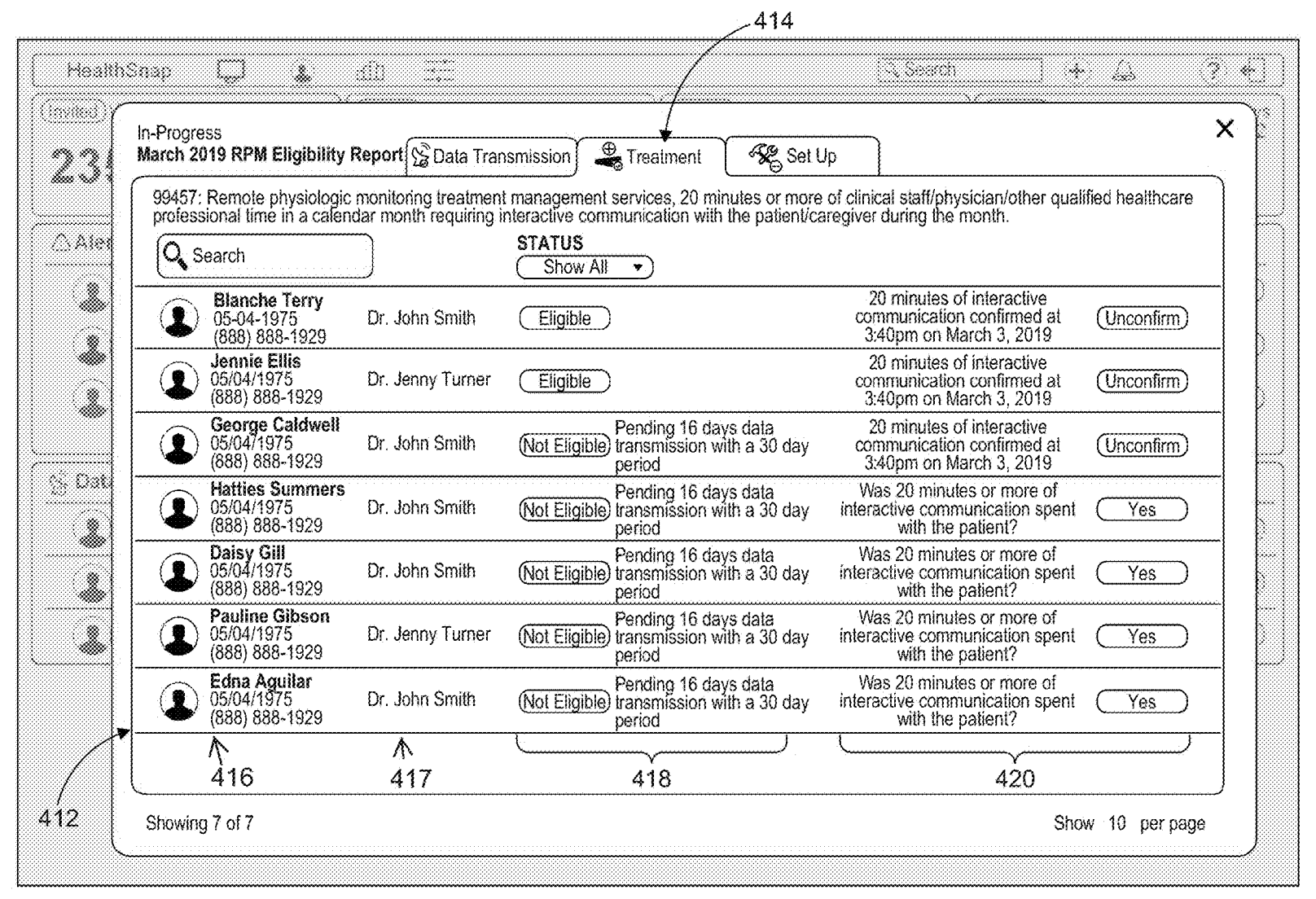

With reference to FIG. 4B, in response to selecting the "View Progress" button, as described above, a pop up 412 may be rendered. The pop up 412 may include a progress report GUI for the treatment reimbursement 414 for each of the healthcare provider's patients. The progress report GUI for the treatment reimbursement 414 may include a list of the patients' names, date of birth, and phone number in a first column 416, the ordering provider in a second column 417, the eligibility status for each respective patient in a third column 418, and a confirmation or unconfirmation button in a fourth column 420. The eligibility status in the third column 418 may be, for example, and without limitation, "Eligible" or "Not Eligible". A healthcare provider may be eligible for a treatment reimbursement for a patient in response to a healthcare provider providing interactive communication with a patient for a specified amount of time within the given time window. In the event the healthcare provider is not eligible for a treatment reimbursement for a given patient, a text-based reason may be rendered adjacent to the eligibility status in the third column 418. The confirmation or unconfirmation button in the fourth column 420 may be selected to confirm or reverse a confirmation that a healthcare provider has provided interactive communication with a patient for a specified amount of time within the given time window.

Figure 4C:
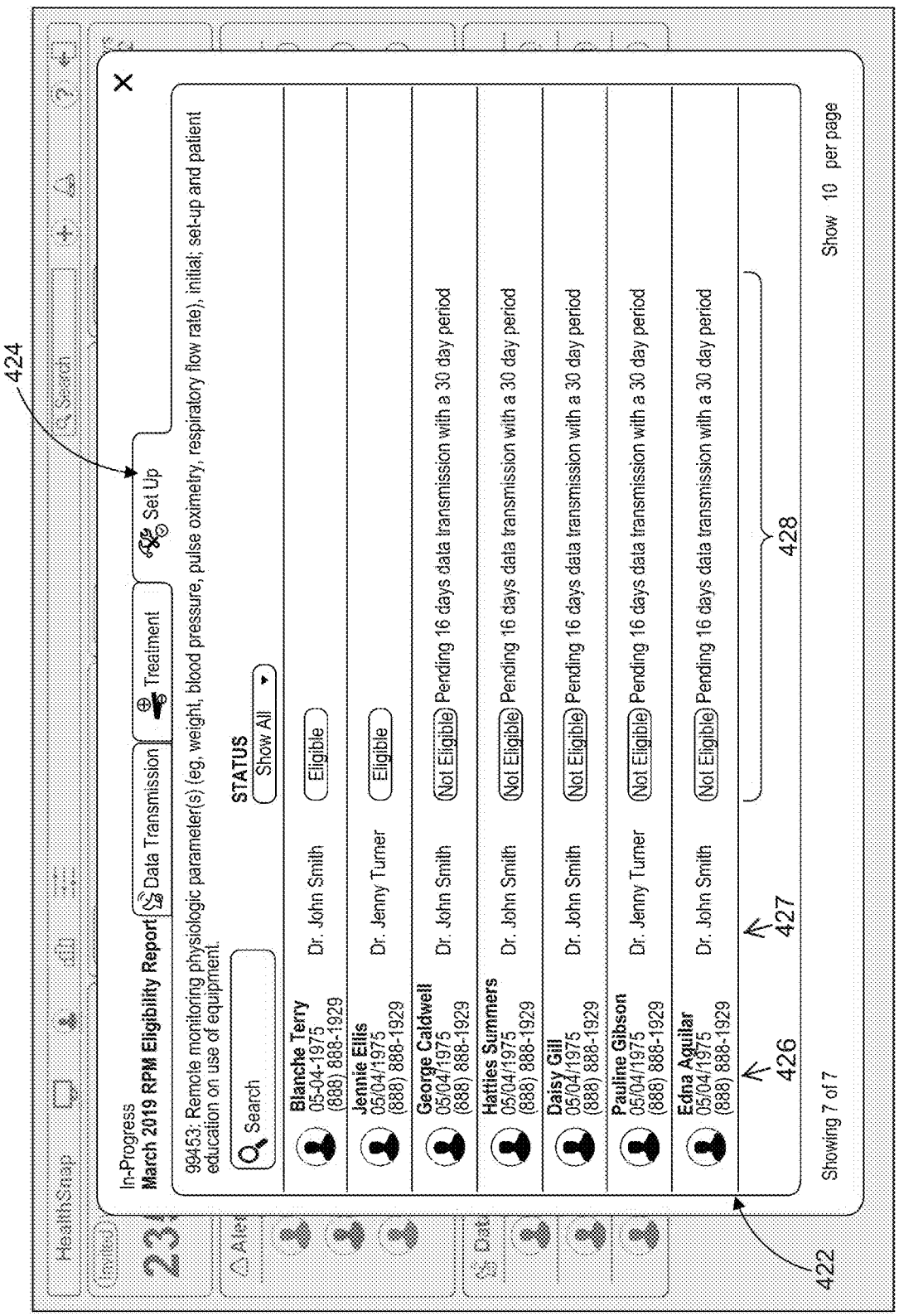

With reference to FIG. 4C, in response to selecting the "View Progress" button as described above, a pop up 422 may be rendered. The pop up 422 may include a progress report GUI for the set up reimbursement 424 for each of the healthcare provider's patients. The progress report GUI for the set up reimbursement 424 may include a list of the patients' names, date of birth, and phone number in a first column 426, an ordering provider in a second column 427, and the eligibility status in a third column 428 for each respective patient. The eligibility status in the third column 428 may be, for example, and without limitation, "Eligible" or "Not Eligible". A healthcare provider may be eligible for a set up reimbursement for a patient, in response to a patient transmitting a minimum threshold number of days within a given time window, for a first time. In the event the healthcare provider is not eligible for a set up reimbursement for a given patient, a text-based reason may be rendered adjacent to the eligibility status in the third column 428.

On the last day of a calendar month, the eligibility reports for that calendar month may be ready to be reviewed and submitted. The eligibility reports may include eligibility reports for data transmission reimbursement, set up reimbursement, and/or treatment reimbursement. The eligibility reports may be reviewed in any order.

With reference to FIG. 4D, in response to selecting the "Review & Submit" button as described above with respect to FIG. 3, a pop up 430 (or first screen) may be rendered, allowing a user to review and submit the eligibility report for the given calendar month. The pop up 430 may include an eligibility report GUI for the data transmission reimbursement 431 for each of the healthcare provider's patients. The eligibility report GUI for the data transmission reimbursement 431 may include a list of the patients' names, phone number, and date of birth in a first column 432, an ordering provider in a second column 433, the eligibility status for each respective patient in a third column 434, a view calendar button in a fourth column 436, and a "Next" button 438. The eligibility status may be, for example, and without limitation, "Eligible" or "Not Eligible". In the event the healthcare provider is not eligible for a data transmission reimbursement for a given patient, a text-based reason may be rendered adjacent to the eligibility status in the third column 434. In the event the healthcare provider is eligible for a data transmission reimbursement for a given patient, a date when eligibility was triggered may be rendered adjacent to the eligibility status in the third column 434. In response to selecting the view calendar button for a given patient in the fourth column 436, a calendar indicating the data transmissions in a calendar month for a patient may be rendered. The eligibility report GUI for the data transmission reimbursement 431 may also include a check-box 437 for indicating that by checking the box 437, the healthcare provider is acknowledging that the information indicated in the eligibility report for the data transmission reimbursement 431 is accurate and truthful. In response to completing the check-box 437, the "Next" button 438 may become selectable, and a healthcare provider may select the "Next" button 438.

With reference to FIG. 4E, in response to receiving a selection of the "Next" button on the pop up 430 (or first screen), a pop up 440 (or second screen) may be rendered, allowing the user to review the setup reimbursement eligibility information. The pop up 440 may include an eligibility report GUI for the set up reimbursement 441 for each of the healthcare provider's patients. The eligibility report GUI for the set up reimbursement 441 may include a list of the patients' names, date of birth, and phone number in a first column 442, an ordering provider in a second column 443, and the eligibility status for each respective patient in a third column 444. The eligibility status in the second column 428 may be, for example, and without limitation, "Eligible" or "Not Eligible". In the event the healthcare provider is not eligible for a set up reimbursement for a given patient, a text-based reason may be rendered adjacent to the eligibility status in the third column 444. In the event the healthcare provider is eligible for a set up reimbursement for a given patient, a date when eligibility was triggered may be rendered adjacent to the eligibility status in the third column 444. The eligibility report GUI for the set up reimbursement 441 may also include a check-box 445 for indicating that by checking the box 445, the healthcare provider is acknowledging that the information indicated in the eligibility report GUI for the set up reimbursement 441 is accurate and truthful. In response to completing the check-box 445, the "Next" button 446 may become selectable, and a healthcare provider may select the "Next" button 446. The eligibility report GUI for the set up reimbursement 441 may also include a "Back" button to return to the data transmission eligibility report GUI.

Figure 4F:
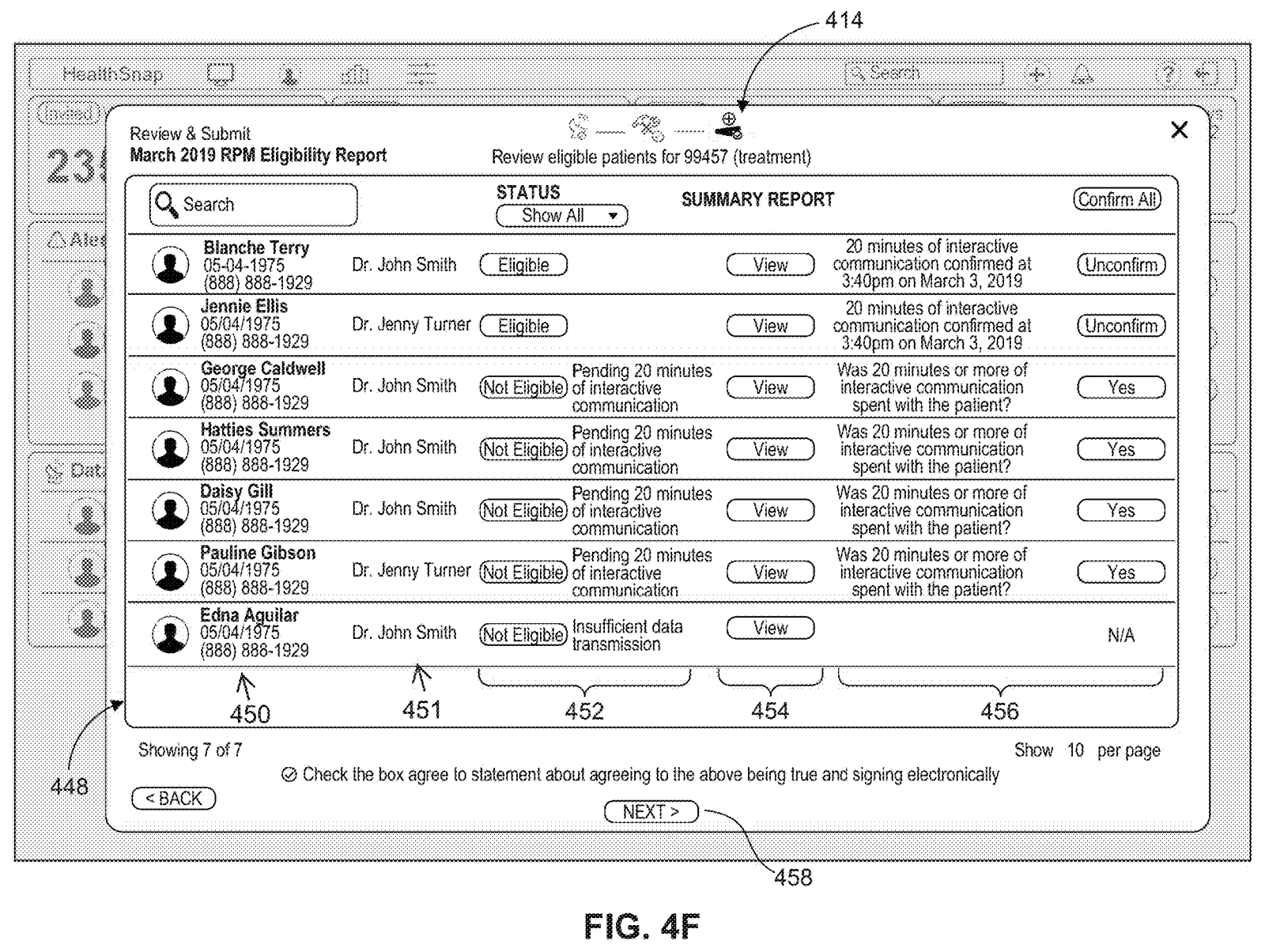

With reference to FIG. 4F, in response to selecting the "Next" button on eligibility report GUI 441 as described above, a pop up 448 (or third screen) may be rendered. The pop up 448 may include an eligibility report GUI for the treatment reimbursement 449 for each of the healthcare provider's patients. The eligibility report GUI for the treatment reimbursement 449 may include a list of the patients' names, date of birth, and phone number in a first column 450, an ordering provider 451, the eligibility status for each respective patient in a third column 452, a view summary report button in a fourth column 454, confirmation or unconfirmation button in a fifth column 456, and a "confirm all" button 457. The eligibility status in the third column 452 may be, for example, and without limitation, "Eligible" or "Not Eligible". In the event the healthcare provider is not eligible for a treatment reimbursement for a given patient, a text-based reason may be rendered adjacent to the eligibility status in the third column 452. In the event the healthcare provider is eligible for a treatment reimbursement for a given patient, a date when eligibility was triggered may be rendered adjacent to the eligibility status in the third column 452. In response to selecting the view summary button in the fourth column 454, a summary report may be rendered for a patient. The summary report may include information about communication with the patient over the past month to determine whether a specified amount of time of interactive communication was provided to the patient. The confirmation or unconfirmation button in the fifth column 456 may be selected to individually confirm or unconfirm that a healthcare provider has provided interactive communication with the listed patient for a specified amount of time within the given time window. The healthcare provider may select the "confirm all" button 457 to confirm with a single selection that each of the patients listed on the eligibility report for the treatment reimbursement 449 were provided a specified amount of time of interactive communication. In response to selecting the "confirm all" button 457, the "confirmation" buttons in the fifth column 456 may be modified to "unconfirmation" buttons. The eligibility report GUI for the treatment reimbursement 449 may also include a check-box 459 for indicating that by checking the box 459, the healthcare provider is acknowledging that the information indicated in the eligibility report for the treatment reimbursement 449 is accurate and truthful. In response to completing the check-box 459, the "Next" button 458 may become selectable, and a healthcare provider may select the "Next" button 458. The eligibility report GUI for the set up reimbursement 441 may also include a "Back" button to return to the set up reimbursement eligibility report GUI (or the data transmission reimbursement eligibility report GUI, if the GUIs are provided in a different order than that given in the present examples).

Figure 4G:
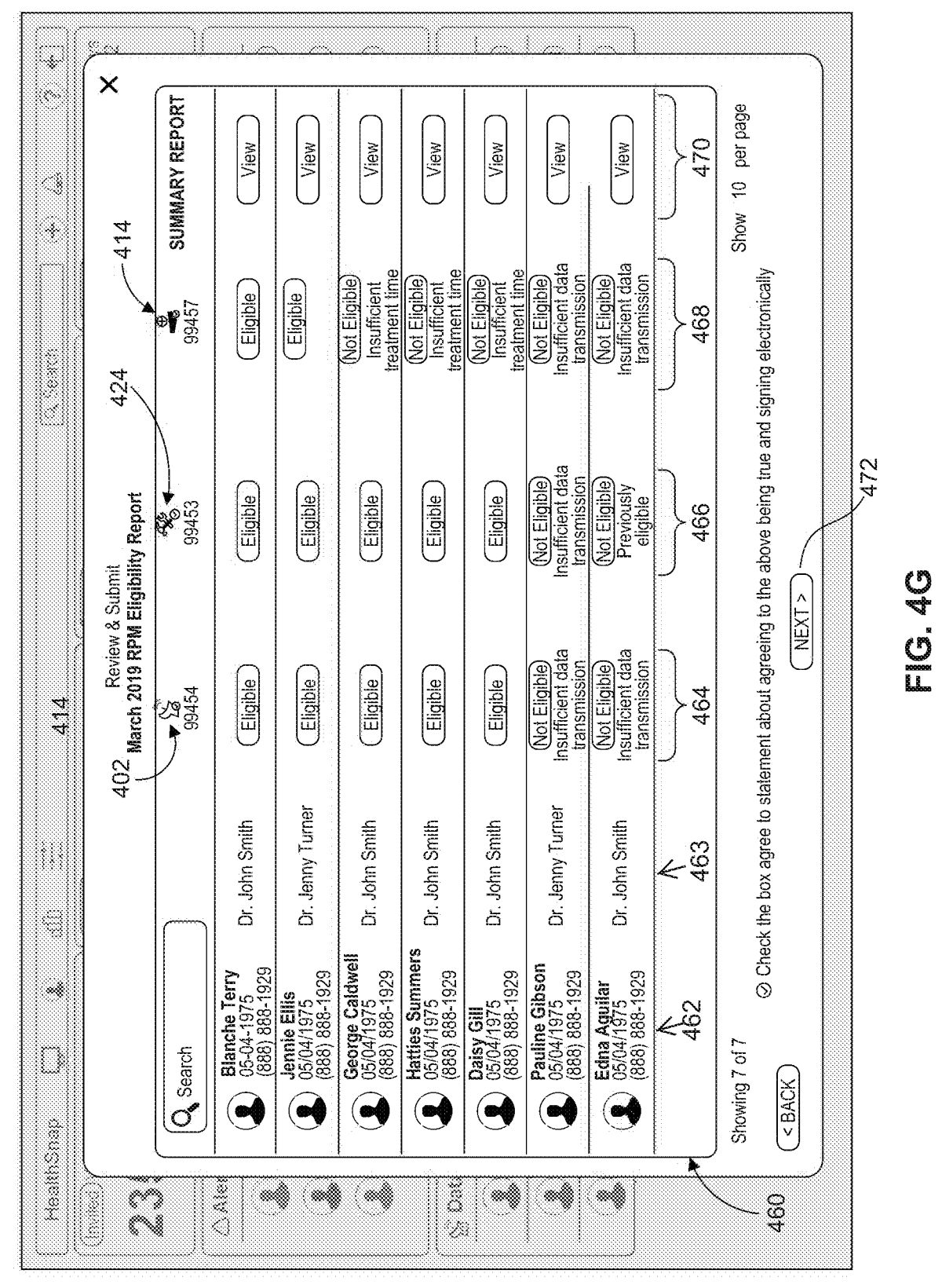

With reference to FIG. 4G, a pop up 460 (or summary screen) providing a summary GUI of the eligibility reports is illustrated. The pop up 460 may include a list of patients' names, date of birth, and phone number in a first column 462, an ordering provider in a second column 463, a data transmission reimbursement eligibility status for each patient in a third column 464, a set up eligibility reimbursement status for each patient in a fourth column 466, a treatment eligibility reimbursement status for each patient in a fifth column 466, and a view summary report button for each patient in a sixth column 470. The summary of the eligibility reports may also include a check-box 471 for indicating that by checking box 471, the healthcare provider is acknowledging that the information indicated in the summary of eligibility reports is accurate and truthful. In response to completing the check-box 471, the "Submit" button 472 may become selectable, and a healthcare provider may select the "Submit" button 472. The summary of eligibility reports may also include a "Back" button to return to the data transmission, treatment, or set up reimbursement eligibility report GUIs.

With reference to FIG. 4H, in response to selecting the "Submit" button 472 in popup 460, the eligibility reports may be submitted, and a popup 474 listing submitted eligibility reports may be rendered. The pop up 474 (or submit screen) may include a list of patients' names, date of birth, and phone number in a first column 476, an ordering provider in a second column 477, a data transmission reimbursement eligibility status for each patient in a third column 478, a set up eligibility reimbursement status for each patient in a fourth column 480, a treatment eligibility reimbursement status for each patient in a fifth column 482, and a view summary report button for each patient in a sixth column 484.

Figure 5A:
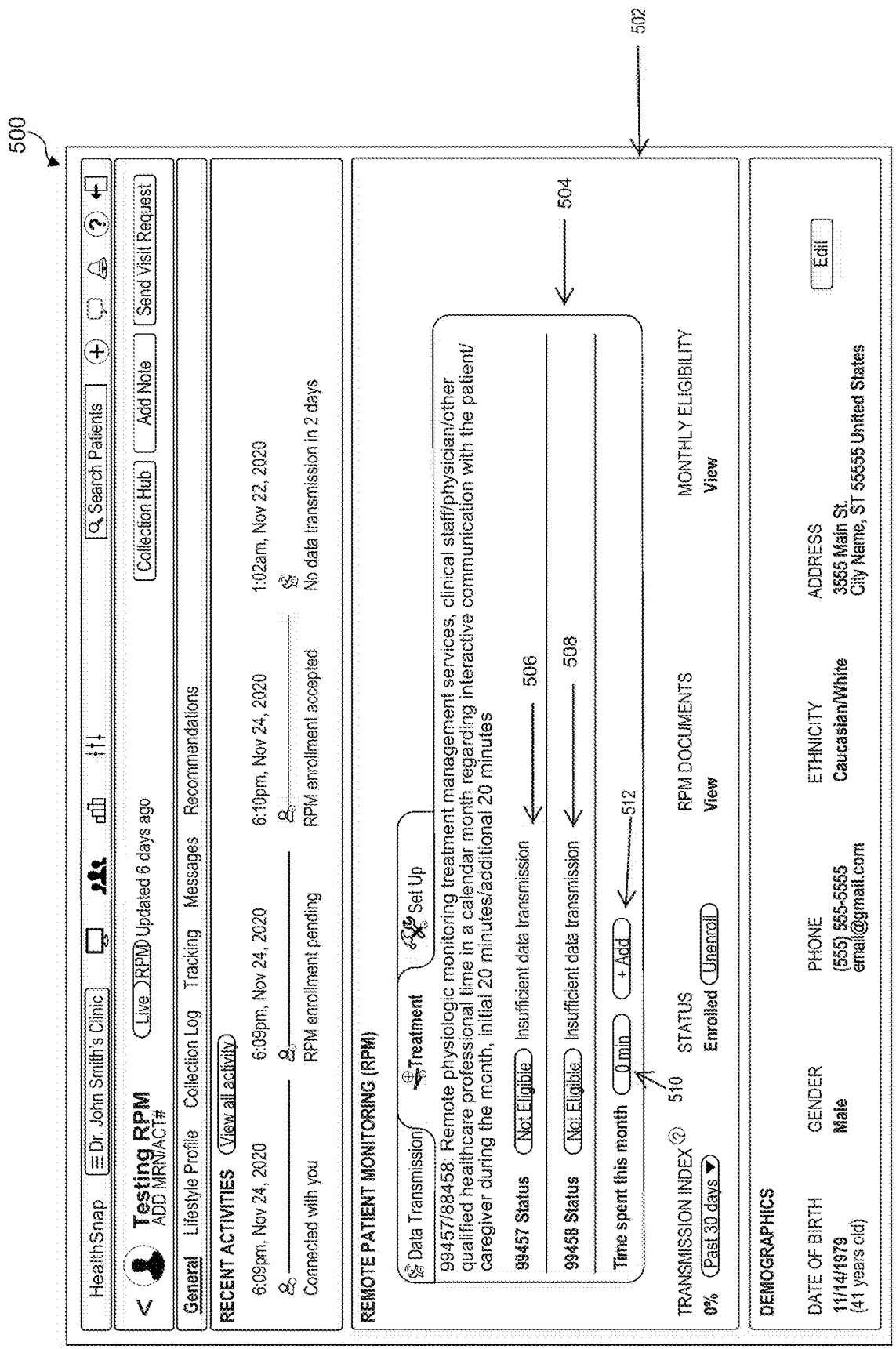

FIGS. 5A-5D are example GUIs allowing users to input an amount of time that healthcare was provided to a patient, according to an example embodiment. With reference to FIG. 5A, a user profile GUI 500 may provide user information to an entity implementing the system for generating an eligibility report. User profile GUI 500 may be similar to user profile GUI 100, shown in FIG. 1; however, user profile GUI 500 allows a user to input time that healthcare was provided to a patient.

As described above, some treatment reimbursement eligibility requires that that healthcare has been provided to a given patient for a certain amount of time. For example, the healthcare provider may confirm that 20 minutes or more of clinical staff/physician/other qualified healthcare professional time in a calendar month have been provided. To report an amount of time that healthcare has been provided, a user may interface with RPM section 502 on user profile GUI 500.

RPM section 502 may be similar to RPM section 106, as shown in FIG. 1; however, RPM section 502 may include a treatment tab 504, which allows users to add input an amount of time that healthcare was provided to a patient. For example, treatment tab 504 may include a treatment reimbursement status 506 and 508. Treatment reimbursement status 506 and 508 may indicate whether a healthcare professional is eligible for a treatment reimbursement for a given patient. In the event that a threshold amount of time of providing healthcare has not been provided to the given patient, the treatment reimbursement status 506 and 508 may indicate that the healthcare professional is "not-eligible" for the treatment reimbursement.

Treatment tab 504 may also include a time GUI element 510. Time GUI element 510 may indicate an amount of time a healthcare provider has provided healthcare to a patient over a period of time. For example, time GUI element 510 may indicate that a healthcare provider has provided 0 minutes of healthcare to the given patient this month. Treatment tab 504 may also include an add button 512 adjacent to time GUI element 510. A user may select add button 512 to add time a healthcare provider has provided healthcare to the given patient.

Figure 5B:
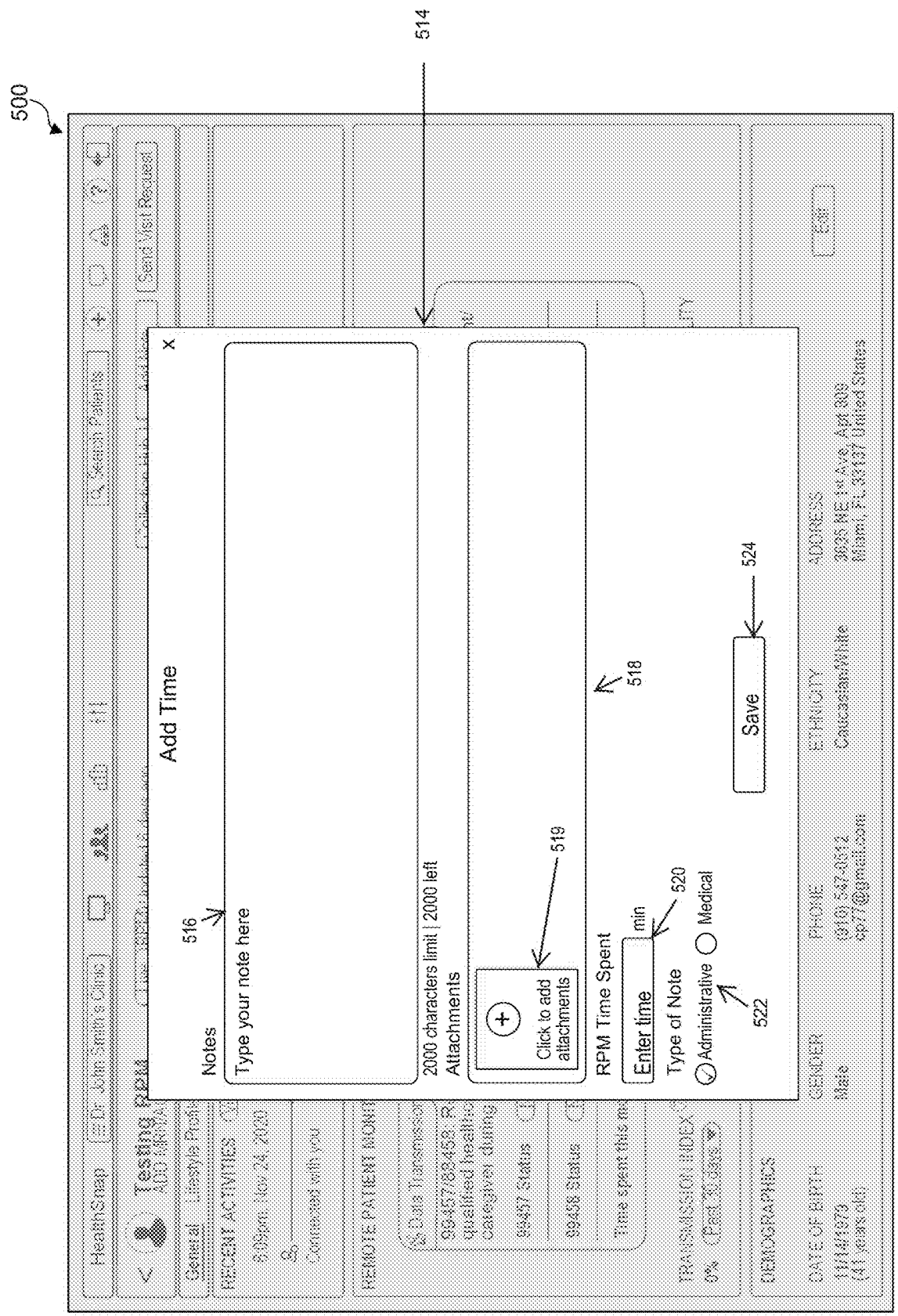

With reference to FIG. 5B, in response to a user selecting add button 512, an add time popup 514 may be rendered over user profile GUI 500. Add time popup 514 may include notes section 516, attachment section 518, enter time input box 520, type of note radio buttons 522, and a save button 524.

A user may input notes about healthcare provided to the given patient in notes section 516. Notes section 516 may accept alphanumeric input. Notes section 516 may have a character limit.

A user may add attachments such as pictures, videos, documents, charts, graphs, or the like about the health of or healthcare provided to the given patient in attachment section 518. The user may select the add attachments button 519 to add an attachment. An icon of an added attachment may be rendered in attachment section 518.

A user may input an amount of time healthcare was provided to the given patient in time input box 520. Time input box 520 may accept numerical input corresponding to a unit of time (e.g., seconds, minutes, hours, etc.).

A user may specify the type of healthcare that was provided to the given patient using type of note radio buttons 522. Type of note radio buttons may include administrative or medical radio buttons. The user may select the radio button that corresponds to the type of healthcare that was provided to the given patient.

A user may save the notes, attachments, amount of time, and selected radio button by selecting save button 524. In response to selecting save button 524, time GUI element 510 may be updated by adding the newly added amount of time to the previously reflected time. For example, if the previously reflected time was 10 minutes and an entry of 5 minutes was added using add time popup 514, time GUI element 510 may indicate that 15 minutes of healthcare has been provided to a given patient.

With reference to FIG. 5C, a healthcare provider's portal GUI 550 is illustrated. Healthcare provider's portal GUI 550 includes a patient's profile (e.g., name, biographical information, demographics information, connected devices, notes, etc.) viewable by a healthcare provider.

Healthcare provider's portal GUI 550 may include a notes section 552. Notes section 552 may indicate notes by a healthcare provider. For example, notes section 552 may include a note 554 to add an amount of time healthcare was provided to a given patient. For example, note 554 may instruct the healthcare provider to add 5 administrative minutes of healthcare that was provided to the given patient in November 2020. A user can edit or delete note 554. Moreover, the user can add additional notes in notes section 554.

With reference to 5D, a treatment eligibility report GUI 560 is illustrated. The treatment eligibility report GUI 560 may be similar to pop up 412, as shown in FIG. 4, including a progress report GUI for the treatment reimbursement 414, as shown in FIG. 4, for each of the healthcare provider's patients.

Treatment eligibility report GUI 560 may also include a time spent column 561. Time spent column 561 includes a time GUI element 562 and an add time button 564. Time GUI element 562 may indicate an amount of time spent providing healthcare to each respective patient over a period of time (e.g., 10 minutes in a month).

A user may select add time button 564 to add an amount of time spent providing healthcare to a given patient. In response to selecting add time button 564, add time popup 514 or a similar popup may be rendered to add an amount of time spent providing healthcare to a patient. In response to adding an entry of an amount of time, time GUI element 562 may be updated by adding the newly added amount of time to the previously reflected time. For example, if the previously reflected time was 10 minutes, and an entry of 5 minutes was added, time GUI element 562 may indicate 15 minutes of healthcare has been provided to a given patient.

Figure 6:
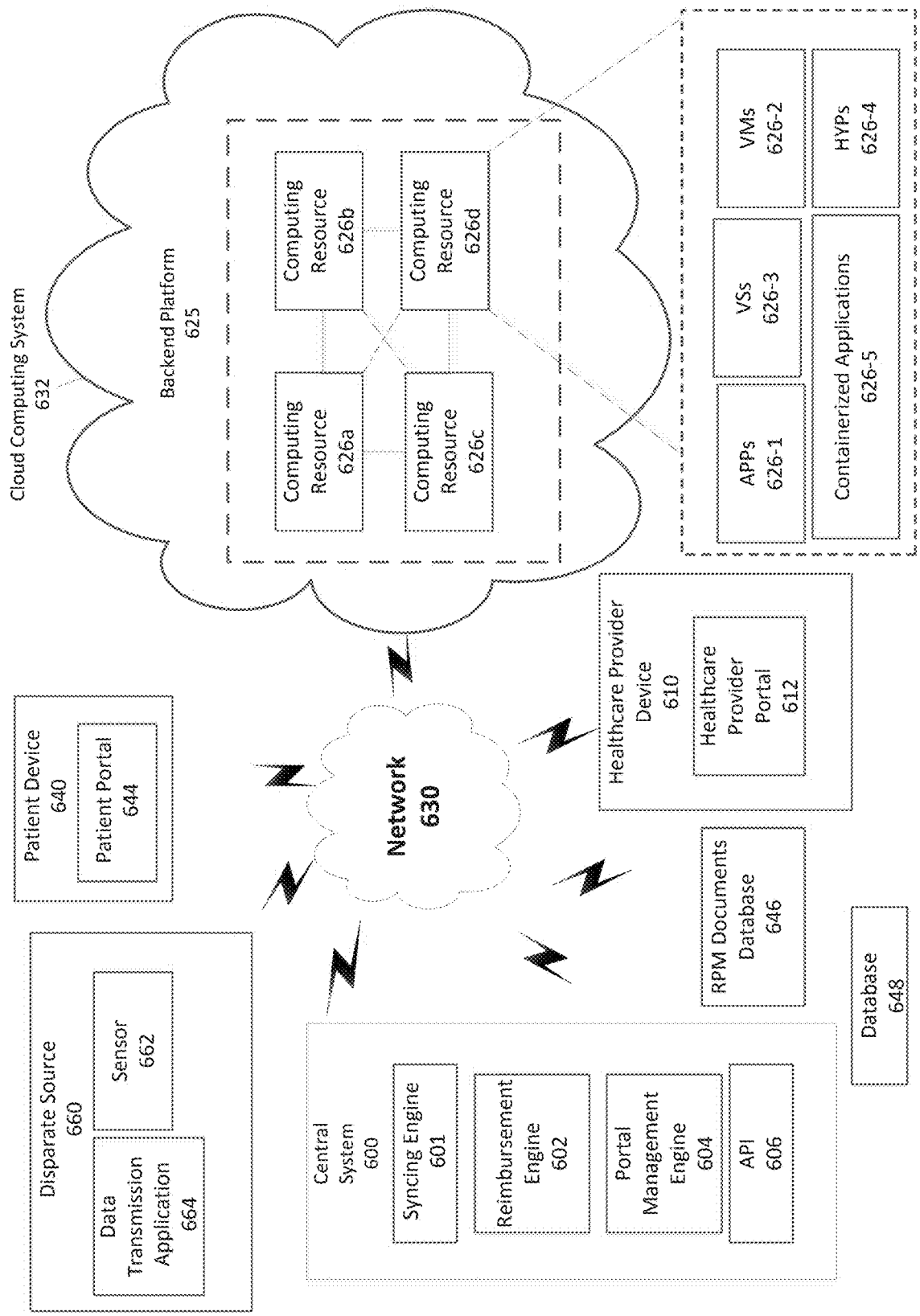
FIG. 6 is a block diagram of an example environment in which systems and/or methods described herein may be implemented according to an example embodiment.
Figure 7:
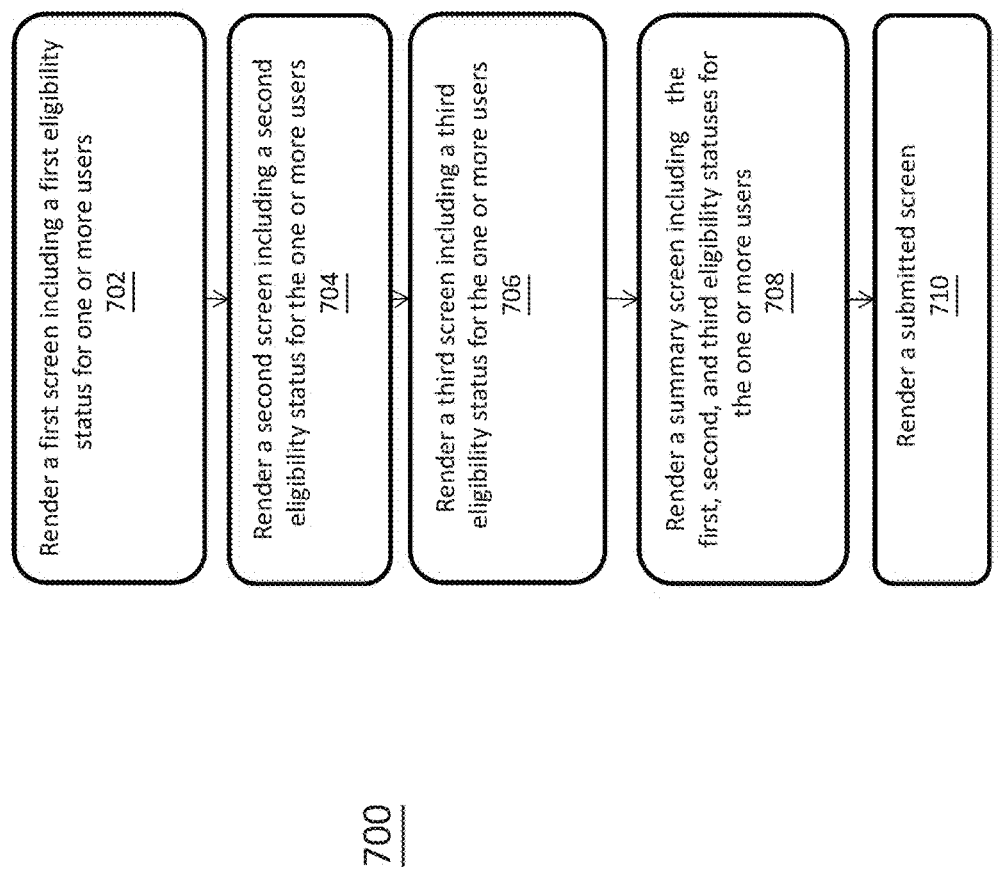
FIG. 7 is a flowchart illustrating processes implemented by a system for rendering a graphical user interface (GUI) for generating an eligibility report according to an example embodiment.

FIG. 6 is a block diagram of an example environment in which systems and/or methods described herein may be implemented. The environment may include a central system 600, a healthcare provider device 610, a patient device 640, a remote patient monitoring ("RPM") documents database 646, a database 648, a backend platform 625, a cloud computing environment 632, multiple disparate sources 660, and a network 630. The devices within the environment may be connected through wired connections, wireless connections, or a combination of wired and wireless connections. The central system 600 may reside fully or partially on the cloud computing system 632 or may be a standalone system. The central system may include a syncing engine 601, a reimbursement engine 602, and the portal management engine 604. The central system 600 may further include an API 606. The API may be configured to interface with the healthcare provider device 610, the patient device 640, and the disparate sources 660. The patient device 640 may include a portal 644. The healthcare provider device 610 may include a healthcare provider portal 612. The portal 644 and the healthcare provider portal 612 may be websites or executable applications configured to interface with the central system 600.

A disparate source 660 may be a wearable device coupled to a wrist strap, watch, glasses, headband, waistband, and/or the like, or a smart device such as a smartphone or tablet. A disparate source 660 may also be an application executing on a smart device, where the application gathers its own data. The disparate source 660 may include a sensor 662 to measure data for a user and a data transmission application 664. The data transmission application 664 may interface with the central system 600. The sensor 662 may sense, track, and store the measured data for a user. This sensing, tracking, and storing may occur continuously or periodically. The data transmission application 664 may extract the data from the sensor 662. The data transmission application 664 may extract the data from the sensor 662 after a specified amount of time, at intervals, or on the detection of new data being sensed and stored. The data may be health data, including, for example, weight, blood pressure, pulse oximetry, respiratory flow rate, and/or the like.

In an embodiment, the disparate source 660 may be coupled to the patient device 640. Once coupled to the patient device 640, portal 644 may pull the data from sensor 662. Alternatively, the disparate source 660 may operate independently from the patient device 640.

In an example embodiment, one or more portions of the network 630 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

The backend platform 625 may include a server or a group of servers. In an embodiment, the backend platform 625 may be hosted in a cloud computing environment 632. It may be appreciated that the backend platform 625 may not be cloud-based, or may be partially cloud-based. The central system 600 may include one or more devices configured to interface with the backend platform 625.

The cloud computing environment 632 includes an environment that delivers computing as a service, whereby shared resources, services, etc., may be provided to the backend platform 625. The cloud computing environment 632 may provide computation, software, data access, storage, and/or other services that do not require end-user knowledge of a physical location and configuration of a system and/or a device that delivers the services. The cloud computing system 632 may include computer resources 626a-d.

Each computing resource 626a-d includes one or more personal computers, workstations, computers, server devices, or other types of computation and/or communication devices. The computing resource(s) 626a-d may host the backend platform 625. The cloud resources may include compute instances executing in the computing resources 626a-d. The computing resources 626a-d may communicate with other computing resources 626a-d by wired connections, wireless connections, or a combination of wired or wireless connections.

Computing resources 626a-d may include a group of cloud resources, such as one or more applications ("APPs") 626-1, one or more virtual machines ("VMs") 626-2, virtualized storage ("VS") 626-3, one or more hypervisors ("HYPs") 626-4, and one or more containerized applications 626-5.

Application 626-1 may include one or more software applications that may be provided to or accessed by central system 600. Alternatively, the application 626-1 may eliminate a need to install and execute software applications on the patient device 640 or the healthcare provider device 610. The application 626-1 may include software associated with backend platform 625 and/or any other software configured to be provided across the cloud computing environment 632. The application 626-1 may send/receive information from one or more other applications 626-1 by the virtual machine 626-2.

Virtual machine 626-2 may include a software implementation of a machine (e.g., a computer) that executes programs like a physical machine. Virtual machine 626-2 may be either a system virtual machine or a process virtual machine, depending upon the use and degree of correspondence to any real machine by virtual machine 626-2. A system virtual machine may provide a complete system platform that supports execution of a complete operating system (OS). A process virtual machine may execute a single program and may support a single process. The virtual machine 626-2 may execute on behalf of a user and/or on behalf of one or more other backend platforms 625 and may manage the infrastructure of cloud computing environment 632, such as data management, synchronization, or long-duration data transfers.

Virtualized storage 626-3 may include one or more storage systems and/or one or more devices that use virtualization techniques within the storage systems or devices of computing resource 626a-d. With respect to a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how administrators manage storage for end users. File virtualization may eliminate dependencies between data accessed at a file-level and the location where files are physically stored. This may enable optimization of storage use, server consolidation, and/or performance of non-disruptive file migrations.

Hypervisor 626-4 may provide hardware virtualization techniques that allow multiple operations systems (e.g., "guest operating systems") to execute concurrently on a host computer, such as computing resource 626a-d. Hypervisor 626-4 may present a virtual operating platform to the guest operating systems and may manage the execution of the guest operating systems multiple instances of a variety of operating systems and may share virtualized hardware resources.

Containerized applications 626-5 may provide for executing distributed applications without having to launch a VM for each distributed application. Containerized applications 626-5 may be implemented by deploying virtualized application containers on a common OS using a platform. As a non-limiting example, the platform may be a platform provided Docker Inc., of San Francisco, Calif.

In an embodiment, users may transmit data from the disparate sources 660 to the central system 600. The syncing engine 601 and reimbursement engine 604 may identify which predefined actions are triggered based on the data transmissions from the users.

The disparate source 660 associated with a user may execute the data transmission application 664. The data transmission application 664 may extract/pull data from sensor 662 of the disparate source 660. The data transmission application 664 may generate a data transmission, including the data pulled from the sensor 662. The data transmission application 664 may attempt to transmit the data transmission from the disparate source 660 to the central system 600. In response to attempting to transmit the data transmission from the disparate source 660 to the central system, the data transmission application 664 may embed a timestamp indicating the date and time of the attempted data transmission and a disparate source identifier in the data transmission. Additionally or alternatively, a timestamp may be added to or may be already associated with each data element within the data transmission based on a time that the data was generated, collected, or received by the sensor 662. In an embodiment, the data transmission application 664 may automatically transmit the data transmission to the central system 600 after collecting a specified amount of data.

The API 606 may receive the data transmission from the data transmission application 664. Each of the data transmissions may include one or more timestamps and a disparate source identifier. The API 606 may receive data transmissions from multiple different disparate sources. Each disparate source may be associated with the same or a different user. Additionally, the API 606 may receive multiple data transmissions from the same disparate source 660 of a single user.

The syncing engine 601 may determine a date and time corresponding to the data in the data transmission from the disparate source 660 based on the timestamp. As an example, a disparate source 660 may not transmit (e.g., may attempt and fail to transmit) a data transmission as scheduled when the disparate source 660 has limited network connectivity (e.g., during airplane travel), such that the data transmission is not completed until a later date. The syncing engine 601 may determine the appropriate time or date to ascribe to the data based on the timestamp so that the data transmission is accounted for the day the disparate source 660 generated, collected, or received the data or made an attempt to send the data, rather than the day when the data transmission was actually completed. The data may be stored in the database 648, based on the time stamp and the disparate source ID.

The reimbursement engine 602 may identify eligibility for predefined actions to be triggered by the data reimbursements based on the timestamp of the data transmission for a given user. A first eligibility status may correspond with a predefined action of a first type. A second eligibility status may correspond with a predefined action of a second type. A third eligibility status may correspond with a predefined action of a third type. The reimbursement engine 602 may designate the first eligibility status as eligible in response to receiving data transmissions from the given user accounted for a specified amount of days within a given time period, and after a specified amount of days since a last instance, the first eligibility status was designated as eligible for the given user or since the date of user's enrollment. The reimbursement engine 602 may designate the second eligibility status as eligible in response to receiving a first data transmission from a user. The reimbursement engine 602 may designate the third eligibility status as eligible in response to receiving data transmissions from the given user accounted for a specified amount of days within a given time period, and after a specified amount of days since a last instance, the first eligibility status was designated as eligible for the given user or since the date of the user's enrollment and interactive communication with the user for a certain amount of time over a given time period. The eligibility statuses may be stored in database 648.

The portal management engine 604 may receive data from the healthcare provider portal 612 to generate eligibility reports for a given calendar month. The portal management 604 may retrieve the first, second, and third eligibility statuses for each user over the given calendar month from the database 648. The portal management engine 604 may render a first screen of a graphical user interface (GUI) including names of one or more users, a first eligibility status corresponding to a first type of predefined action for each of the one or more users, and a button to view a calendar for each of the one or more users.

The portal management engine 604 may receive a first input indicating verification of the first eligibility status for each of the one or more users rendered on the first screen. In response to receiving the first input, the portal management engine 604 may render a second screen of the GUI including each of the one or more users' names and a second eligibility status corresponding to a second type of predefined action for each of the one or more users.

The portal management engine 604 may receive a second input indicating verification of the second eligibility status for each of the one or more users rendered on the second screen. In response to receiving the second input, the portal management engine 604 may render a third screen of the GUI including each of the one or more users' names, a third eligibility status corresponding to a third type of predefined action for each of the one or more users, an indication of whether a qualifying factor for the eligibility status of the third type has been satisfied for each one of the one or more users.

The portal management engine 604 may receive a third input indicating verification of the third eligibility status for each of the one or more users rendered on the third screen. In response to receiving the third input, the portal management engine 604 may render a summary screen of the GUI, including the first, second, and third eligibility status for each of the one or more users. The summary screen may include a submit button. In response to the actuation of a submit button rendered on the summary screen, the portal management engine 604 may render a submitted screen including the names of the one or more users, the first, second, and third eligibility statuses, and a submission timestamp, wherein in response to the actuation of the submit button. In response to the actuation of the submit button, the portal management engine 604 may lock the values associated with the first, second, and third eligibility statuses stored in the database 648 to make them un-editable.

An example implementation use case follows, based on the architecture of FIG. 6, according to an embodiment of the invention. A healthcare provider may execute the healthcare provider portal 612 using the healthcare provider device 610. The healthcare provider portal 612 may provide healthcare provider information. The healthcare provider portal 612 may provide the ability to generate and transmit RPM enrollment invitations to patients. The healthcare provider portal 612 may provide a selection of data that the healthcare provider would like to monitor for the patient. The data may be one or more of, for example, and without limitation, body weight, height, body fat, resting heart rate, blood pressure, VO2max, and/or the like. Prior to sending the invitation, the healthcare provider portal 612 may prompt the healthcare provider to provide various types of information such as a medically-necessary RPM enrollment reason, a diagnosis, and an ordering provider. Such information may be input via a variety of interface features such as a dropdown menu containing prepopulated selections, a free input box, radio buttons, and/or the like. The ordering provider may be entered, for example, using a dropdown menu of provider names. In an embodiment, the healthcare provider may upload a comma-separated values (CSV) file, including information about the patient(s) to be invited. The patient name, contact information, reason for RPM enrollment, and diagnosis may be extracted from the CSV file and auto-populated into input boxes and dropdown menus. The invitation may be sent to the patient in an email, including a link or Short Messaging Service (SMS) message, including a link.

Once a patient is invited to enroll in RPM, a patient's profile page may be generated on the healthcare provider portal 612 along with an associated status. For example, the healthcare provider portal 612 may render the RPM status as "Pending" on the patient profile page. An activity may be created for "RPM enrollment pending". The healthcare provider may send reminders to the patient or cancel the invitation using the healthcare provider portal 612. The patient profile page may also include a section for RPM documents to be stored. RPM documents may include documentation containing, for example, reasons for RPM enrollment, diagnosis, insurance information, consent forms, and/or the like. The patient profile page may also include information about the patient's connected disparate source 660. The healthcare provider portal 612 may provide to the healthcare provider a patient list, including enrolled, invited, and pending patients.

In response to launching the patient portal 644 by actuating the invitation link or otherwise, the portal 644 may render a popup requesting that the patient enrolls in RPM. Portal 644 may provide various options to the patient, such as options to select "Enroll" or select "I do not want to enroll". If the patient selects "I do not want to enroll", the healthcare provider receives a notification that the patient has denied the invitation to enroll in RPM. If the patient does not answer the invitation within a given time frame, they will receive an email and push notification reminder on the patient portal 612. In the event that the patient selects the "I do not want to enroll" option, for example, portal 644 may render reasons on why they should enroll in RPM. The reasons are customizable by the healthcare provider using the healthcare provider portal 612.

In response to selecting to enroll in RPM, portal 644 may prompt the patient to complete various fields, such as full name, date of birth, and phone number. Portal 644 may prompt the patient to agree to consent statements. Portal 644 may prompt the patient to agree that their provider has ordered the RPM for the reason the provider has given and voluntarily give their informed consent to enroll in and participate in the RPM program with the ordering provider. Portal 644 may prompt the patient to agree to a second statement accepting the terms of use. Each signature may be, for example, an e-signature. Once the patient has completed the consent forms, the RPM enrollment is complete. The patient's RPM status may be changed to "Enrolled." The healthcare provider may receive an email and/or a notification on the healthcare provider portal 612 that the patient has enrolled.

Once the patient is enrolled in RPM, the patient's disparate source 660 may send data transmissions, including health data, to the central system 600. The sensor 660 may sense, track, and measure the health data of the patient. The data transmission application 664 may extract/pull the health data from the sensor 662. For example, the data transmission application 664 may extract/pull the health data every 24 hours. Alternatively, sensor 660 may push the health data to the data transmission application 664 continuously or periodically. The data transmission application 664 may form a health dataset from the health data. The health dataset may be transmitted to the central system 600 using the data transmission application 664. In an embodiment, the data transmission application 664 may automatically transmit the health dataset to the central system 600 after collecting a specified amount of health data. Additionally or alternatively, the data transmission application 664 may transmit the health dataset to the central system 600 upon request by either the patient or the central system 600.

The API 606 may receive the data transmission from the data transmission application 664. Each of the data transmissions may include one or more time stamps. In embodiments, the API 606 may receive health datasets from multiple different disparate sources of the same patient and/or from multiple different disparate sources of various patients. In some embodiments, the API 606 may receive multiple health datasets from the same disparate source 660 corresponding to the single patient.

The syncing engine 601 may determine whether the health data is in a correct format. For example, the health data may be received in JavaScript Object Notation (JSON) data-interchange format or eXtensible Markup Language (XML) format. The syncing engine 601 may determine whether the data format is acceptable by the database 648. In the event the health data is not in the correct format, the syncing engine 601 may normalize the data into a format accepted by the database 648. The healthcare data may include a disparate source ID from which the healthcare data was transmitted. The syncing engine 601 may determine the patient associated with the healthcare data using the disparate source ID. For example, the syncing engine 601 may correlate the disparate source ID in the healthcare data with the disparate source ID of the disparate source 660 tied to the patient. The reimbursement engine 602 may store the healthcare data in the database 648 such that it is correlated to the patient record(s).

The syncing engine 601 may determine a date and time for the healthcare data from the disparate source 660 based on the timestamp(s). The timestamp(s) may be generated when the data is generated, collected, or received by the disparate source and/or at the time the disparate source 660 first attempted to transmit the data transmission. The healthcare data may be stored in the database 648 based on the timestamp and the disparate source ID. In this way, sequential data collected continuously or periodically by a disparate source but transmitted asynchronously to a central location can be ordered properly when combined with other sequential data received at the central location from other disparate sources.

The reimbursement engine 602 may determine whether the healthcare provider is eligible for any reimbursement based on the received healthcare data. For example, in response to receiving the certain number of data transmissions from the patient, the reimbursement engine 602 may determine that the healthcare provider is eligible for the set up reimbursement.

The reimbursement engine 602 may also track of frequency and amount of days of data transmissions from the patient. The reimbursement engine 602 may determine the healthcare provider is eligible for the data transmission reimbursement in response to determining there have been a minimum number of days of data transmissions for a patient in a specified time window and after a specified amount of days after the previous data transmission reimbursement eligibility was triggered or a specified amount of days after the date of enrollment.

The reimbursement engine 602 may also determine whether a healthcare provider is eligible for the treatment reimbursement. For example, a healthcare provider may use the healthcare provider portal 612 to confirm that healthcare has been provided for a certain amount of time. For example, the healthcare provider may confirm that 20 minutes or more of clinical staff/physician/other qualified healthcare professional time in a calendar month have been provided. In response to receiving the confirmation, the reimbursement engine 602 may determine that the healthcare provider is eligible for treatment reimbursement for that patient.

The portal management engine 604 may render GUIs for the healthcare provider portal 612 and portal 644. For example, the portal management engine 604 may generate and render a data transmission GUI on the healthcare provider portal 612. The data transmission GUI may track data transmissions received from patients and indicate eligibility of a predefined action such as a data transmission reimbursement based on the data transmissions. The portal management engine 604 may generate and render eligibility report GUIs on the healthcare provider portal 612, as shown in FIGS. 4A-4H and FIG. 5D.

FIG. 1 is a flowchart illustrating a process 700 implemented by a system for rendering a graphical user interface (GUI) for generating eligibility reports. It is to be appreciated the operations may occur in a different order, and some operations may not be performed.

In operation 702, a central system may render a first screen of a graphical user interface (GUI), including names of one or more users, a first eligibility status corresponding to a first type of predefined action for each of the one or more users, and a button to view a calendar for each of the one or more users. This first screen may be, for example, pop up 430 as described above with respect to FIG. 4D.

In operation 704, the central system may render a second screen of the GUI including each of the one or more users' names and a second eligibility status corresponding to a second type of predefined action for each of the one or more users. The second screen is rendered in response to receiving a first input indicating verification of the first eligibility status for each of the one or more users rendered on the first screen. The second screen may be, for example, pop up 440 as described above with respect to FIG. 4E.

In operation 706, the central system may render a third screen of the GUI including each of the one or more users' names, a third eligibility status corresponding to a third type of predefined action for each of the one or more users, and an indication of whether a qualifying factor for the eligibility status of the third type has been satisfied for each one of the one or more users. The third screen is rendered in response to receiving a second input indicating verification of the second eligibility status for each of the one or more users rendered on the second screen. The third screen may be, for example, pop up 448 as described above with respect to FIG. 4F.

In operation 708, the central system may render a summary screen of the GUI, including the first, second, and third eligibility status for each of the one or more users. The summary screen is rendered in response to receiving a third input indicating verification of the third eligibility status for the one or more users rendered on the third screen. The summary screen may be, for example, pop up 460 as described above with respect to FIG. 4G.

In operation 710, in response to the actuation of a submit button rendered on the summary screen, the central system may display a submitted screen including the names of the one or more users, the first, second, and third eligibility statuses, and a submission timestamp. In response to the actuation of the submit button, values associated with the first, second, and third eligibility statuses stored in a database are un-editable. The submitted screen may be, for example, pop up 474 as described above with respect to FIG. 4H.

Figure 8:
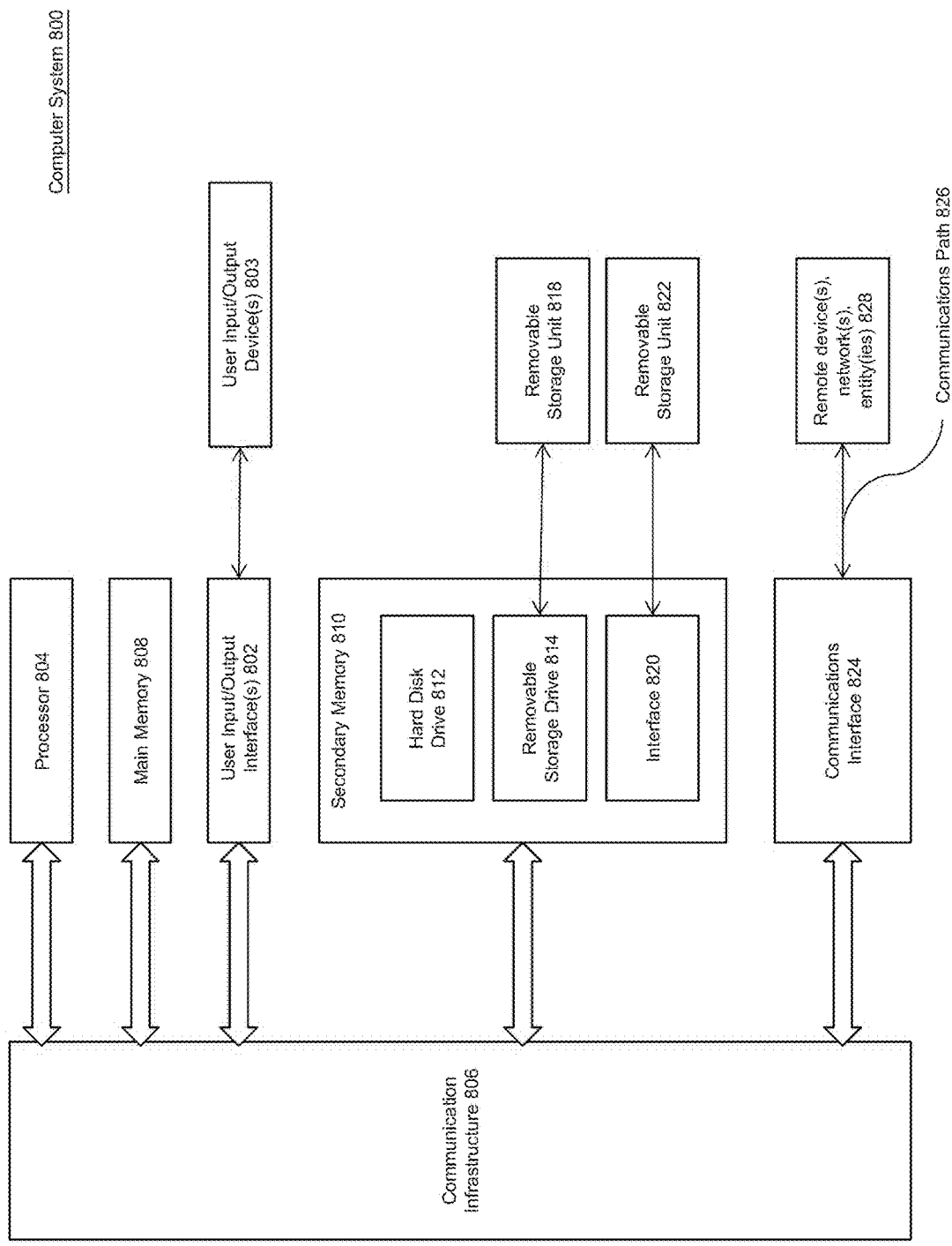
FIG. 8 is a block diagram of example components of a computing system according to an embodiment according to an example embodiment.

FIG. 8 is a block diagram of example components of device 800. One or more computer systems 800 may be used, for example, to implement any of the embodiments discussed herein, as well as combinations and sub-combinations thereof. Computer system 800 may include one or more processors (also called central processing units, or CPUs), such as a processor 804. Processor 804 may be connected to a communication infrastructure or bus 806.

Computer system 800 may also include user input/output device(s) 803, such as monitors, keyboards, pointing devices, etc., which may communicate with communication infrastructure 806 through user input/output interface(s) 802.

One or more of processors 804 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 800 may also include a main or primary memory 808, such as random access memory (RAM). Main memory 808 may include one or more levels of cache. Main memory 808 may have stored therein control logic (i.e., computer software) and/or data.

Computer system 800 may also include one or more secondary storage devices or memory 810. Secondary memory 810 may include, for example, a hard disk drive 812 and/or a removable storage device or drive 814.

Removable storage drive 814 may interact with a removable storage unit 818. Removable storage unit 818 may include a computer usable or readable storage device having stored thereon computer software (control logic) and/or data. Removable storage unit 818 may be program cartridge and cartridge interface (such as that found in video game devices), a removable memory chip (such as an EPROM or PROM) and associated socket, a memory stick and USB port, a memory card and associated memory card slot, and/or any other removable storage unit and associated interface. Removable storage drive 814 may read from and/or write to removable storage unit 818.

Secondary memory 810 may include other means, devices, components, instrumentalities or other approaches for allowing computer programs and/or other instructions and/or data to be accessed by computer system 800. Such means, devices, components, instrumentalities or other approaches may include, for example, a removable storage unit 822 and an interface 820. Examples of the removable storage unit 822 and the interface 820 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 800 may further include a communication or network interface 824. Communication interface 824 may enable computer system 800 to communicate and interact with any combination of external devices, external networks, external entities, etc. (individually and collectively referenced by reference number 828). For example, communication interface 824 may allow computer system 800 to communicate with external or remote devices 828 over communications path 826, which may be wired and/or wireless (or a combination thereof), and which may include any combination of LANs, WANs, the Internet, etc. Control logic and/or data may be transmitted to and from computer system 800 via communication path 826.

Computer system 800 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 800 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 800 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 800, main memory 808, secondary memory 810, and removable storage units 818 and 822, as well as tangible articles of manufacture embodying any combination of the foregoing. Such control logic, when executed by one or more data processing devices (such as computer system 800), may cause such data processing devices to operate as described herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

The foregoing description of the specific embodiments will so fully reveal the general nature of the invention that others may, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for rendering a graphical user interface (GUI) for generating a report, the method comprising:
   rendering, by one or more computing devices, a first screen of a graphical user interface (GUI) including names of one or more users, a first status corresponding to a first type of predefined action for each of the one or more users, and a selector to view a calendar for each of the one or more users;
   rendering, by the one or more computing devices, a second screen of the GUI including each of the one or more users' names and a second status corresponding to a second type of predefined action for each of the one or more users, wherein the second screen is rendered in response to receiving a first input indicating verification of the first status for each of the one or more users;
   rendering, by the one or more computing devices, a third screen of the GUI including each of the one or more users' names, a third status corresponding to a third type of predefined action for each of the one or more users, and an indication of whether a qualifying factor for the third status has been satisfied for each one of the one or more users, wherein the third screen is rendered in response to receiving a second input indicating verification of the second status for each of the one or more users; and
   rendering, by the one or more computing devices, a summary screen of the GUI including the first, second, and third statuses for each of the one or more users, wherein the summary screen is rendered in response to receiving a third input indicating verification of the third status for each one of the one or more users, wherein the first, second, and third statuses of the one or more users are included in an eligibility report for a given calendar month.

2. The method of claim 1, further comprising:
   rendering, by the one or more computing devices, the names of the one or more users in first column of the first screen;
   rendering, by the one or computing devices, the first status corresponding to the first type in a second column of the first screen; and
   rendering, by the one or more computing devices, the selector to view a calendar in a third column of the first screen.

3. The method of claim 2, wherein the first status is designated as eligible for a given user in response to receiving data transmissions from the given user for a specified number of days within a given time period and after a specified number of days since a last time the first status was designated as eligible for the given user.

4. The method of claim 3, wherein in response to actuating the selector to view a calendar, the method further comprises rendering, by the one or more computing devices, a popup indicating a history of data transmissions of the given user over the given period of time.

5. The method of claim 1, further comprising:
   rendering, by the one or more computing devices, the names of the one or more users in first column of the second screen; and
   rendering, by the one or computing devices, the second status corresponding to the second type of predefined action for each of the one or more users in a second column of the second screen.

6. The method of claim 1, further comprising:
   rendering, by the one or more computing devices, the names of the one or more users in first column of the third screen; and
   rendering, by the one or computing devices, the third status corresponding to the third type of the one or more users in a second column of the third screen.

7. The method of claim 6, in response to actuation of a submit button rendered on the summary screen, the method further comprising: rendering, by the one or more computing devices, a submitted screen including the names of the one or more users, the first, second, and third statuses, and a submission timestamp, wherein in response to actuation of the submit button, values associated with the first, second, and third statuses for the given calendar month stored in a database are designated as un-editable.

8. A system for rendering a graphical user interface (GUI) for generating a report, the system comprising:
   a memory;
   a processor coupled to the memory, the processor configured to:
      render a first screen of a graphical user interface (GUI), including names of one or more users, a first status corresponding to a first type of predefined action for each of the one or more users, and a selector to view a calendar for each of the one or more users;
      render a second screen of the GUI including each of the one or more users' names and a second status corresponding to a second type of predefined action for each of the one or more users, wherein the second screen is rendered in response to receiving a first input indicating verification of the first status for each of the one or more users;
      render a third screen of the GUI including each of the one or more users' names, a third status corresponding to a third type of predefined action for each of the one or more users, and an indication of whether a qualifying factor for the third eligibility status has been satisfied for each one of the one or more users, wherein the third screen is rendered in response to receiving a second input indicating verification of the second status for each of the one or more users; and render a summary screen of the GUI including the first, second, and third statuses for each of the one or more users, wherein the summary screen is rendered in response to receiving a third input indicating verification of the third status for each one of the one or more users, wherein the first, second, and third statuses of the one or more users are included in an eligibility report for a given calendar month.

9. The system of claim 8, wherein the processor is further configured to:
render the names of the one or more users in first column of the first screen;
render the first status corresponding to the first type in a second column of the first screen; and
render the selector to view a calendar in a third column of the first screen.

10. The system of claim 8, wherein the first status is designated as eligible for a given user in response to receiving data transmissions from the given user for a specified number of days within a given time period and after a specified number of days since a last time the first status was designated as eligible for the given user.

11. The system of claim 8, wherein in response to actuating the selector to view a calendar, the processor is further configured to render a popup indicating a history of data transmissions of the given user over the given period of time.

12. The system of claim 8, wherein the processor is further configured to:
render the names of the one or more users in first column of the second screen; and
render the second status corresponding to the second type of predefined action for each of the one or more users in a second column of the second screen.

13. The system of claim 1, wherein the processor is further configured to:
render the names of the one or more users in first column of the third screen; and
render the third status corresponding to the third type of the one or more users in a second column of the third screen.

14. The method of claim 13, in response to actuation of a submit button rendered on the summary screen, the processor further configured to render a submitted screen including the names of the one or more users, the first, second, and third statuses, and a submission timestamp, wherein in response to actuation of the submit button, values associated with the first, second, and third statuses for the given calendar month stored in a database are designated as un-editable.

15. A non-transitory computer-readable medium having instructions stored thereon that, when executed by at least one computing device, cause the at least one computing device to perform operations comprising:
rendering a first screen of a graphical user interface (GUI) including names of one or more users, a first status corresponding to a first type of predefined action for each of the one or more users, and a selector to view a calendar for each of the one or more users;

rendering a second screen of the GUI including each of the one or more users' names and a second status corresponding to a second type of predefined action for each of the one or more users, wherein the second screen is rendered in response to receiving a first input indicating verification of the first status for each of the one or more users;

rendering a third screen of the GUI including each of the one or more users' names, a third status corresponding to a third type of predefined action for each of the one or more users, and an indication of whether a qualifying factor for the third status has been satisfied for each one of the one or more users, wherein the third screen is rendered in response to receiving a second input indicating verification of the second status for each of the one or more users; and rendering a summary screen of the GUI including the first, second, and third statuses for each of the one or more users, wherein the summary screen is rendered in response to receiving a third input indicating verification of the third status for each one of the one or more users, wherein the first, second, and third statuses of the one or more users are included an eligibility report for a given calendar month.

16. The non-transitory medium of claim 15, the operations further comprising:
rendering the names of the one or more users in first column of the first screen;
render the first status corresponding to the first type in a second column of the first screen; and
render the selector to view a calendar in a third column of the first screen.

17. The non-transitory medium of claim 16, wherein the first status is designated as eligible for a given user in response to receiving data transmissions from the given user for a specified number of days within a given time period and after a specified number of days since a last time the first status was designated as eligible for the given user.

18. The non-transitory medium of claim 17, wherein in response to actuating the selector to view a calendar, the operations further comprise rendering a popup indicating a history of data transmissions of the given user over the given period of time.

19. The non-transitory medium of claim 15, the operations further comprising:
rendering the names of the one or more users in first column of the second screen; and
render the second status corresponding to the second type of predefined action for each of the one or more users in a second column of the second screen.

20. The non-transitory medium of claim 15, further comprising:
render the names of the one or more users in first column of the third screen; and
render the third status corresponding to the third type of the one or more users in a second column of the third screen.

* * * * *